US010813597B2

(12) United States Patent
Rice et al.

(10) Patent No.: US 10,813,597 B2
(45) Date of Patent: Oct. 27, 2020

(54) NON-INVASIVE HEMODYNAMIC ASSESSMENT VIA INTERROGATION OF BIOLOGICAL TISSUE USING A COHERENT LIGHT SOURCE

(71) Applicants: The Regents of the University of California, Oakland, CA (US); Covidien LP, Mansfield, MA (US)

(72) Inventors: Tyler Bywaters Rice, Irvine, CA (US); Michael Ghijsen, Irvine, CA (US); Bruce J. Tromberg, Irvine, CA (US); Bruce Yee Yang, Irvine, CA (US); Sean Michael White, Irvine, CA (US)

(73) Assignees: THE REGENTS OF THE UNIVERSITY OF CALIFORNIA, Oakland, CA (US); COVIDIEN LP, Mansfield, MA (US)

( * ) Notice: Subject to any disclaimer, the term of this patent is extended or adjusted under 35 U.S.C. 154(b) by 527 days.

(21) Appl. No.: 15/488,263

(22) Filed: Apr. 14, 2017

(65) Prior Publication Data
US 2018/0296168 A1 Oct. 18, 2018

(51) Int. Cl.
*A61B 5/026* (2006.01)
*A61B 5/021* (2006.01)
(Continued)

(52) U.S. Cl.
CPC .......... *A61B 5/7278* (2013.01); *A61B 5/0261* (2013.01); *G02B 27/48* (2013.01);
(Continued)

(58) Field of Classification Search
CPC ... A61B 5/7278; A61B 5/0261; A61B 5/7275; A61B 5/02007; A61B 5/029; A61B 5/726; A61B 5/1455; A61B 5/1464
See application file for complete search history.

(56) References Cited

U.S. PATENT DOCUMENTS 5,372,136 A  12/1994 Steuer et al.
5,499,627 A  3/1996 Steuer et al.
(Continued)

FOREIGN PATENT DOCUMENTS

WO  WO 2015/176294  11/2015

OTHER PUBLICATIONS

Dunn et al. "Comparison of speckleplethysmographic (SPG) and photoplethysmographic (PPG) imaging by Monte Carlo simulations and in vivo measurements" Biomedical Optics Express, vol. 9, No. 9, Sep. 1, 2018, pp. 4306-4316. (Year: 2018).*
(Continued)

*Primary Examiner* — Angela M Hoffa
(74) *Attorney, Agent, or Firm* — Nguyen Tarbet

(57) ABSTRACT

Systems and methods are disclosed for determining physiological information in a subject. The system includes: a light source positionable along a first location outside of the subject; a photo-sensitive detector positionable along a second location outside of the subject and configured to detect scattered light and generate a signal; a processor having a program and a memory, wherein the processor is operably coupled to the detector and configured to receive and store the signals generated over a period of time; wherein the processor is programmed to derive contrast metrics from the stored signals, calculate a waveform from the contrast metrics, decompose the waveform into basis functions and respective amplitudes, and compare the basis function amplitudes to determine the physiological information.

22 Claims, 16 Drawing Sheets

(51) Int. Cl.
*A61B 5/029* (2006.01)
*A61B 5/00* (2006.01)
*G02B 27/48* (2006.01)
*A61B 5/1455* (2006.01)
*A61B 5/02* (2006.01)

(52) U.S. Cl.
CPC ........... *A61B 5/021* (2013.01); *A61B 5/02007* (2013.01); *A61B 5/029* (2013.01); *A61B 5/14551* (2013.01); *A61B 5/4875* (2013.01); *A61B 5/726* (2013.01); *A61B 5/7257* (2013.01)

(56) References Cited

U.S. PATENT DOCUMENTS

| | | | |
|---|---|---|---|
| 5,533,511 A * | 7/1996 | Kaspari | A61B 5/02007 128/925 |
| 6,253,097 B1 | 6/2001 | Aronow et al. | |
| 7,113,817 B1 | 9/2006 | Winchester, Jr. et al. | |
| 7,596,412 B1 * | 9/2009 | Kroll | A61B 5/02028 607/18 |
| 8,855,749 B2 * | 10/2014 | McKenna | G06K 9/00557 600/473 |
| 10,070,796 B2 * | 9/2018 | Ostroverkhov | A61B 5/6815 |
| 2002/0095075 A1 | 7/2002 | Madarasz et al. | |
| 2004/0127779 A1 | 7/2004 | Steuer et al. | |
| 2004/0220480 A1 | 11/2004 | Braeuer et al. | |
| 2005/0089243 A1 | 4/2005 | Ludwig | |
| 2005/0143662 A1 | 6/2005 | Marchitto et al. | |
| 2006/0224073 A1 * | 10/2006 | Lin | A61B 5/02007 600/513 |
| 2006/0281992 A1 | 12/2006 | Stothers et al. | |
| 2008/0183059 A1 | 7/2008 | LaPlante et al. | |
| 2008/0188726 A1 | 8/2008 | Presura et al. | |
| 2008/0188728 A1 | 8/2008 | Neumann et al. | |
| 2008/0234590 A1 | 9/2008 | Akkermans et al. | |
| 2009/0118623 A1 | 5/2009 | Serov et al. | |
| 2010/0014724 A1 * | 1/2010 | Watson | A61B 5/00 382/128 |
| 2010/0155577 A1 | 6/2010 | Kiesel et al. | |
| 2010/0168585 A1 | 7/2010 | Fujii et al. | |
| 2011/0013002 A1 * | 1/2011 | Thompson | A61B 5/0059 348/77 |
| 2011/0026783 A1 | 2/2011 | Fujii et al. | |
| 2012/0071769 A1 | 3/2012 | Dunn et al. | |
| 2012/0095354 A1 | 4/2012 | Dunn et al. | |
| 2012/0130215 A1 | 5/2012 | Fine et al. | |
| 2012/0162438 A1 | 6/2012 | Thakor et al. | |
| 2012/0232363 A1 | 9/2012 | Al-Ali et al. | |
| 2012/0301839 A1 | 11/2012 | Stoianovici | |
| 2013/0204112 A1 | 8/2013 | White et al. | |
| 2014/0049779 A1 | 2/2014 | Tin et al. | |
| 2014/0206976 A1 | 7/2014 | Thompson et al. | |
| 2016/0073959 A1 * | 3/2016 | Eagle | A61B 5/02152 600/486 |
| 2016/0206247 A1 * | 7/2016 | Morland | A61B 5/7207 |
| 2017/0156678 A1 * | 6/2017 | Lim | A61B 5/7232 |
| 2017/0311815 A1 * | 11/2017 | Yu | A61B 5/6826 |
| 2018/0106897 A1 * | 4/2018 | Shouldice | A61B 5/7264 |
| 2019/0086316 A1 * | 3/2019 | Rice | A61B 5/0075 |
| 2019/0167124 A1 * | 6/2019 | Verkruijsse | A61B 5/7221 |

OTHER PUBLICATIONS

Ghijsen et al. "Wearable speckle plethysmography (SPG) for characterizing microvascular flow and resistance." Biomedical Optics Express, vol. 9, No. 8, Aug. 1, 2018, pp. 3937-3952. (Year: 2018).*
Humeau-Heurtier et al. "Relevance of Laser Doppler and Laser Speckle Techniques for Assessing Vascular Function: State of the Art and Future Trends." IEEE Transactions on BME, vol. 60, No. 3, Mar. 2013, pp. 659-666. (Year: 2013).*
Dun, J.F., et al. A Transmissive Laser Speckle Imaging Technique for Measuring Deep Tissue Blood Flow: An Example Application in Finger Joints; Lasers in Surgery and Medicine; vol. 43; pp. 21-28; published 2011.
International Search Report for International Application No. PCT/US17/25979 dated Jun. 21, 2017.
International Search Report for International Application No. PCT/US17/28178 dated Jul. 13, 2017.

* cited by examiner

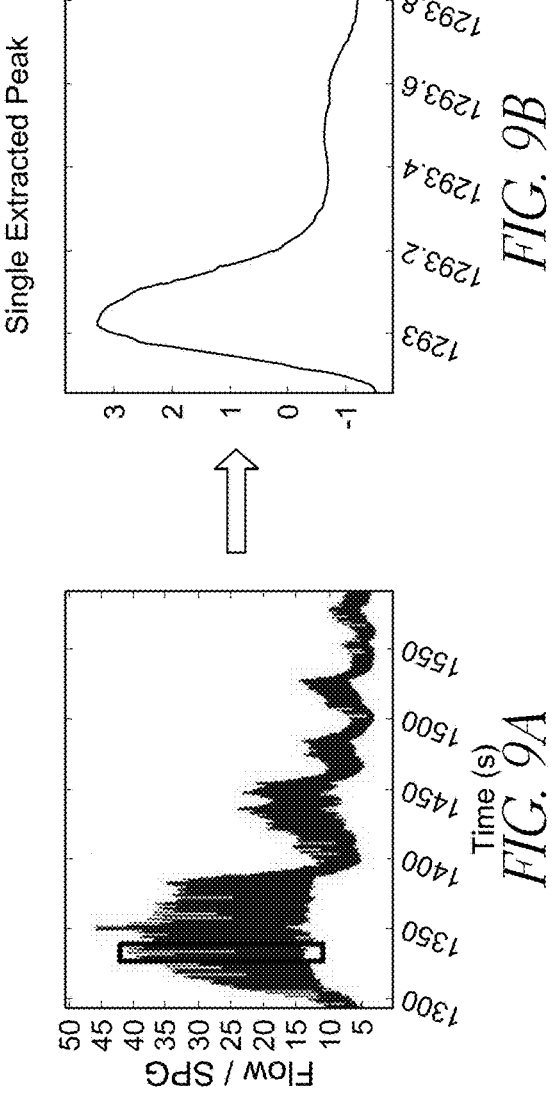
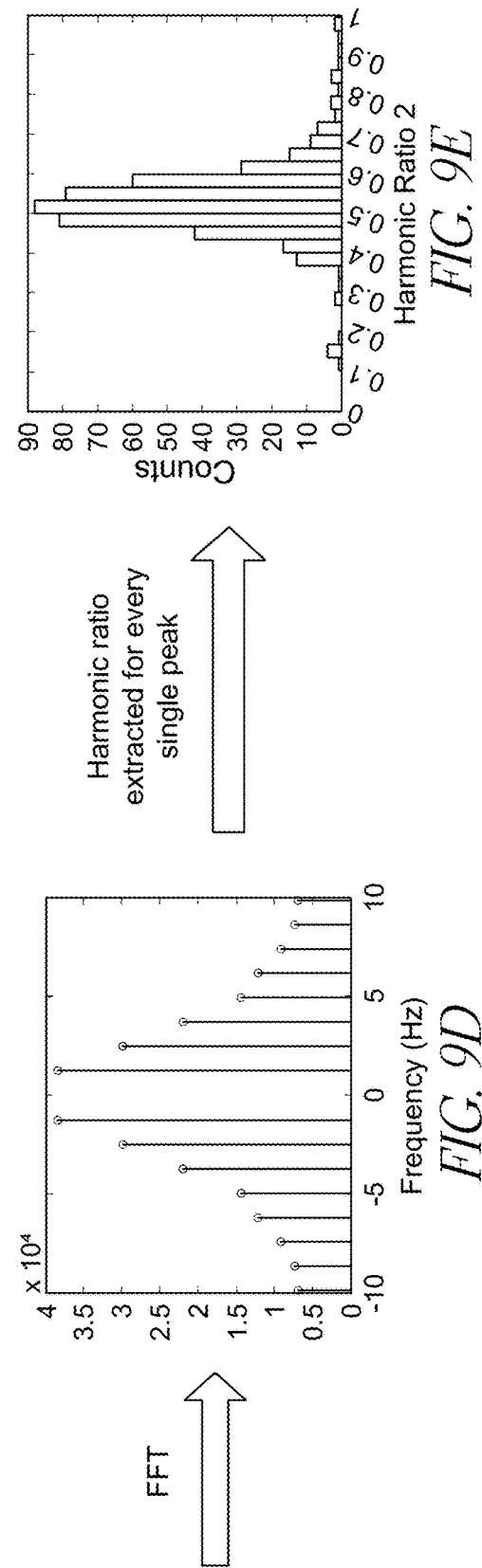

NON-INVASIVE HEMODYNAMIC ASSESSMENT VIA INTERROGATION OF BIOLOGICAL TISSUE USING A COHERENT LIGHT SOURCE

STATEMENT REGARDING FEDERALLY SPONSORED R&D

This invention was made with Government support under Grant No. EB015890, awarded by the National Institutes of Health. The Government has certain rights in this invention.

BACKGROUND

Field

Embodiments of the disclosure relate to noninvasive medical monitoring and methods for obtaining non-invasive measurements of physiological parameters, including hemodynamic parameters such as blood pressure and arterial compliance.

Description of the Related Art

Noninvasive hemodynamic monitoring refers to techniques that measure and characterize in some way the physiological and pathological state of the cardiovascular system without cannulating a vessel or introducing harmful radiation or substances to the subject. Examples include methods that aim to measure blood pressure, cardiac output, vascular tone, arterial stiffness or fluid status. These methods have the potential to improve inpatient and outpatient healthcare, in addition to opening up new research directions and revolutionizing wearable devices for personal health and fitness.

One method of noninvasive hemodynamic monitoring is Photoplethysmography (PPG), which is an optical technique that measures microvascular expansion caused by the pulsatile component of blood pressure. This can be achieved by interrogating tissue with visible and near infrared light. PPG instrumentation consists of a light source to illuminate the tissue and a photodetector to measure small fluctuations in light intensity. These dynamics are then transformed mathematically into the PPG signal which is representative of blood volume expansion due to the pulse. PPG is the base technology for pulse oximetry where the ratio-metric comparison of PPG amplitude is compared at multiple discrete wavelengths in order to recover arterial oxygen saturation.

Despite the clinical success of pulse-oximetry, PPG has not been successful in other aspects of hemodynamic monitoring. One technique called vascular unloading applies PPG alongside a finger-sized cuff to measure blood pressure non-invasively. Although this device has achieved some level of clinical dissemination, it is highly susceptible to changes in vascular tone in addition to requiring calibration steps to account for differences in central and peripheral blood pressure. Overall, its limited accuracy makes it unsuited for ubiquitous use. Researchers have also used PPG pulse-wave analysis and characterization strategies for a wide variety of hemodynamic monitoring applications including cardiac output, vascular stiffness, venous assessment, and microvascular perfusion, to name a few. There has been some success in these ventures, but due to the limited signal quality inherent in the PPG they fail to surpass the threshold of clinical viability

SUMMARY

Laser Speckle Imaging (LSI) is a noncontact optical imaging method that recovers relative blood flow by imaging tissue being illuminated with a coherent light source. Red blood cells moving through the vascular system act as optical scatterers that modulate the spatial coherence distribution of photons interrogating the tissue. In LSI, light remitted from the tissue is most often imaged using a CCD or CMOS camera. Images recorded by the detector contain a pattern referred to as speckle that is due to constructive and destructive interference of coherent light on the detector. The speckle pattern fluctuates at a rate dependent on the degree of motion of the scattering objects. Hence, blood perfusion has a direct effect on the spatial and temporal variance of remitted light. Over finite integration times, the tissue perfusion can be calculated by measuring the level of the variance in one or more collected images.

If performed at a high enough frame-rate, LSI is capable of sampling the heartbeat waveform in the same manner as PPG. The main difference is that LSI is probing the pulsatile component of blood flow velocity whereas PPG is sampling the pulsatile component of vascular volumetric expansion. The pulsatile LSI signal, named here the Speckleplethysmograph (SPG), has several qualities that make it ideal for noninvasive hemodynamic monitoring. First, the signal quality is superior to that of PPG. The total volume modulation during the pulsatile cardiac cycle is relatively small (e.g., less than 2%) and confounded by many variables (e.g., vasoconstriction/dilation, vascular stiffness, Reynold's number, etc.) resulting in a PPG signal with limited physiological information. The small size of the signal also makes the PPG signal especially vulnerable to noise (i.e. a relatively small signal-to-noise ratio). The SPG signal is a physiologically larger signal and is less diluted by noise. For example, a clear SPG signal can be acquired in patient groups where PPG tends to fail, such as in individuals over the age of 50, subjects with peripheral vascular disease, and those experiencing vasoconstriction. The SPG also maintains signal quality during increased vascular tone such as during cold shock or dehydration. This is significant because it is in these cases that the PPG signal becomes overwhelmed by noise. In addition to being a more robust signal than PPG, the SPG offers complimentary information since it is physically interrogating a different phenomenon (PPG represents volumetric expansion whereas SPG represents blood flow).

Various embodiments disclosed herein relate to a new approach for the non-invasive measurement and characterization of physiological parameters. These parameters may include but are not limited to: blood pressure, vascular stiffness, microvascular function, hyper-/hypo-tension, oxygen metabolism, cardiac function, fluid status, hemoglobin concentration, oxygenation, and blood viscosity. The quantitative measurement and/or qualitative characterization of these or other physiological parameters comprise the determination of physiological parameters (i.e. physiological information) about a subject upon which the assessment is performed.

The principle behind embodiments disclosed herein is that the aforementioned physiological parameters can be characterized by information related to the blood flow and blood volume in a given tissue, where the flow and volume may be determined using a coherent light-based imaging system. The coherent light-based imaging system measures speckle signals after interaction with moving scattering objects (i.e. blood cells), and relates the speckle signals to flow and volume. The flow and volume of blood is pulsatile due to the cardiac cycle, and thus is represented by a waveform. The flow and volume waveforms contain valuable information about the hemodynamics of the sample. Embodiments relate to systems and methods for producing and analyzing said waveforms, in order to characterize said physiological parameters.

In one embodiment, coherent light from a light source interrogates a complex turbid medium. The light remitted after propagation through said medium is measured using a photodetector placed in either a transmission or reflectance geometry. Either the light source or detector (or both) may be making contact with the tissue or may be in a noncontact configuration. Using a single light source emitting at least partially coherent light, at least two distinct signals, which are offset in time, may be acquired. One of these signals is the periodic representation of blood flow, which utilizes spatiotemporally varying dynamic scattering information known as the speckle variance. From the variance information, metrics of contrast can be derived and transformed into indices such as but not limited to: speckle contrast and/or the speckle flow index. The signal derived from metrics of contrast will be referred to herein as the Speckleplethysmogram (SPG). A second signal can be obtained through a metric of total light intensity, such as but not limited to the mean intensity of the sensor array. The signal derived from metrics of mean photo-intensity will be referred to herein as the Photoplethysmogram (PPG), and is representative of the volume of light absorbing blood within the sample. The PPG can be derived from the same source of coherent light as the speckle signal.

Within a single instrument, comparisons may be drawn between the SPG and the PPG signals as well as the characterization of each signal individually. For example, embedded within the waveforms are both timing features with respect to each other and intrinsically within the dynamics of the individual signals. Additionally, timing features can be derived from one of many reference signals including but not limited to the PPG and an electrocardiogram (ECG) signal. The SPG signal may be used to extract these timing features in addition to one of the aforementioned reference signals. In the absence of a quality PPG signal or as a substitute for the PPG signal, an ECG signal may be used. Physiological parameters can then be derived from features of the waveform or the comparison between said waveforms. For example, by generating data descriptive of the timing offset between signals and/or by analyzing the offset nature as well as the structure of the individual time-varying signals, one can recover parameters quantifying or characterizing vascular stiffness, blood pressure, and other features not limited to these.

In contrast with other methods, the disclosed systems and methods are based on content-rich information reflective of the complexities of the cardiovascular system. By analyzing the timing offset and SPG waveform information, the methods presented herein gain access to highly informed signals reflecting the complexities of the arterial network. Accordingly, the systems and methods disclosed herein have more potential for greater clinical applicability than other hemodynamic monitoring technologies known in the art.

Another advantage of the disclosed systems and methods is their reliance on the SPG signal, which possesses superior signal over the PPG signal. As mentioned earlier, the SPG maintains signal quality in situations where the PPG concedes to noise such as in patient groups with extensive cardiovascular disease. Importantly, patients with cardiovascular problems are in greatest need of effective monitoring.

A third advantage is that the systems and methods disclosed herein may be practiced with inexpensive component devices that are simple to build and/or easy to operate. In contrast with other methods that measure timing features of cardiovascular system such as pulse-transit-time, embodiments of the methods described herein may be performed with only a single light-source and a single detector.

In some embodiments, a system for determining one or more physiological parameters in a subject is disclosed. The system includes a light source, a photo-sensitive detector, and a processor. The light source is positionable along a first location outside of the subject, and is configured to direct light from the first location toward a plurality of light-scattering particles flowing in pulsatile motion within a blood vessel inside of the subject. The photo-sensitive detector is positionable along a second location outside of the subject, and configured to detect light scattered by the plurality of light-scattering particles and generate a signal related to the detected light. The processor includes a program and a memory and is operably coupled to the photo-sensitive detector. The processor is configured to receive and store in memory the signals generated over a period of time. The processor is programmed to derive contrast metrics from the signals stored in memory over the period of time and calculate a waveform from the contrast metrics. The processor is further programmed to decompose the waveform into one or more characteristic features and make a comparison using the one or more decomposed characteristic features to determine the one or more physiological parameters. The one or more physiological parameters may relate to one or more of atherosclerotic obstruction, vascular compliance, blood pressure, cardiac output, venous status, or vascular tone.

The processor may be further programmed to convert the contrast metrics into metrics of volumetric flow. The one or more characteristic features may be amplitudes of a basis function. The processor may be further programmed to generate a histogram based on a ratio of basis function amplitudes. The one or more characteristic features may be amplitudes of a periodic basis function, and the decomposition may be equivalent to a time-frequency transform. The one or more characteristic features may be amplitudes of a wavelet basis function, and the decomposition may represent a wavelet transform. The one or more characteristic features may be abstract features. The one or more characteristic features can describe the width of the waveform pulse. The one or more characteristic features may be the timing occurrences of local extrema. The one or more characteristic features may be amplitudes of local extrema. The one or more characteristic features may be magnitudes of slopes of the waveform.

In some embodiments, a method for determining one or more physiological parameters from light-scattering particles in pulsatile motion within a physiological system is disclosed. The method comprises positioning a light source at a first site outside of the physiological system and actuating the light source, such that light is directed toward the light-scattering particles. The method further comprises positioning a photo-sensitive detector at a second site outside of the physiological system, wherein the second site is located along a path of light scattered by at least some of the light-scattering particles, and using the photo-sensitive detector to detect light scattered by at least some of the light-scattering particles over a period of time. The method further comprises communicating signals related to the detected light to a processor, deriving intensity values from the communicated signals, and calculating a contrast metric by comparing the intensity. The method further comprises producing a contrast waveform related to the pulsatile motion of the light-scattering particles based on a change in the contrast metric over time, decomposing the contrast waveform into one or more characteristic features, and making a comparison using the one or more decomposed characteristic features. The method also comprises determining the one or more physiological parameters based at least in part on the comparison. The one or more physiological parameters may relate to one or more of atherosclerotic obstruction, vascular compliance, blood pressure, cardiac output, venous status, or vascular tone.

The method may further comprise relating the contrast metric to a metric of volumetric flow. The method may further comprise determining a reference signal of a physiological origin distinct from the contrast metric, wherein making a comparison comprises comparing the contrast waveform to the reference signal. The reference signal can be a photo-intensity metric. The method may further comprise converting the photo-intensity metric into a metric of absorption. Comparing the contrast waveform to the reference signal may comprise comparing temporal locations of a characteristic feature found in both the contrast waveform and the reference signal. The reference signal may be a reference waveform. Comparing the contrast waveform to the reference signal may comprise comparing pulsatile amplitudes of the contrast and reference waveforms. Comparing the contrast waveform to the reference signal may comprise comparing non-pulsatile amplitudes of the contrast and reference waveforms. Comparing the contrast waveform to the reference signal may comprise determining a temporal offset of one or more characteristic features. The reference signal can be an electrocardiogram.

The method may further comprise decomposing the contrast and reference waveforms into basis functions and respective amplitudes. Comparing the contrast waveform to the reference signal may comprise comparing the decomposed contrast and reference waveforms. Comparing the contrast waveform to the reference signal may comprise comparing one or more basis function amplitudes of one decomposed waveform to one or more basis function amplitudes of the other decomposed waveform. Comparing the contrast waveform to the reference signal may comprise comparing one or more ratios of basis function amplitudes of one decomposed waveform to one or more ratios of basis function amplitudes of the other decomposed waveform.

BRIEF DESCRIPTION OF THE DRAWINGS

These and other features, aspects, and advantages of the present disclosure will now be described with reference to the drawings of embodiments, which embodiments are intended to illustrate and not to limit the disclosure. One of ordinary skill in the art would readily appreciate that the features depicted in the illustrative embodiments are capable of combination in manners that are not explicitly depicted, but are both envisioned and disclosed herein.

FIG. 1A shows the system in a reflectance, non-contact configuration. FIG. 1B shows the system in a transmission, non-contact configuration. FIG. 1C shows the system in a reflectance, contact configuration. FIG. 1D shows the system in a transmission, contact configuration.

FIG. 7C illustrates an example of an algorithm for extracting physiological parameters from detector input using a wavelet transform. FIG. 7B depicts an example of a generated SPG signal and scalogram attained under normal conditions. FIG. 7C depicts an example of a generated SPG signal and scalogram attained under post-exercise vasodilation.

FIG. 3A shows the time delay between the signals. FIG. 3B shows the average time delay calculated for four subjects in three different physiological states. FIG. 3C shows the correlation between the measured time delay and subject age.

FIGS. 9A-9E depict a method of deriving physiologically relevant data from an SPG signal. FIG. 9A shows the identification of a single pulse from a raw SPG signal. FIG. 9B shows the extraction of the identified pulse from the raw SPG signal. FIG. 9C shows the appending of the extracted peak onto itself. FIG. 9D shows the generation by a Fast Fourier Transform (FFT) of a frequency spectrum characterizing the harmonic content of the extracted pulse. FIG. 9E shows the generation of a histogram characterizing the distributions of harmonic ratios over a set of pulses extracted from the raw SPG signal.

DETAILED DESCRIPTION

The systems and methods described herein enable the non-invasive recovery of parameters relevant to subject physiology. These parameters may be used along mathematical models to derive non-invasive hemodynamic parameters including but not limited to blood pressure, cardiac output, venous status, hematocrit, and vascular tone. The systems and methods disclosed herein may incorporate component devices, including a light source 100, a photodetector 200 (i.e. a photo-sensitive detector, such as an image sensor), and a processor 500, which may be operatively connected to one another to interrogate a sample 300. In many embodiments, the sample 300 may be a physiological sample, such as a region of tissue on subject, about which physiological information is to be ascertained. The subject may be a living animal, such as a human. The component devices may be standard devices employed in new configurations, methodologies, and/or systems or they may be devices specifically designed or adapted to perform in the systems and methods disclosed herein. The light source 100 may be configured to emit at least partially coherent light. The light source 100 may be a laser, such as a diode laser. In some embodiments, the light source 100 is a VCSEL laser. The photodetector 200 may comprise one or more light-sensitive elements (e.g. pixels) for detecting light recovered from the light source 100 after interaction with a sample 300. The photodetector 200 may, for example, be a silicon camera sensor. The camera sensor may be of any suitable type, including but not limited to CMOS or CCD image sensors. The photodetector 200 may comprise a slit or aperture for modulating the angle of light (i.e. the amount of light) detected. The photodetector 200 may be configured to generate one or more signals related to the detected light and to transmit these signals to the processor 500. The signals may comprise quantifiable information about the intensity of light detected at one or more pixels at a point in time or over a course of time. In some embodiments, the signals may comprise information about the wavelength(s) of the detected light. The signals may be analog or digital. If the signals are analog they may be subsequently converted into digital signals either before or after being transmitted from the photodetector 200.

Figure 1A:
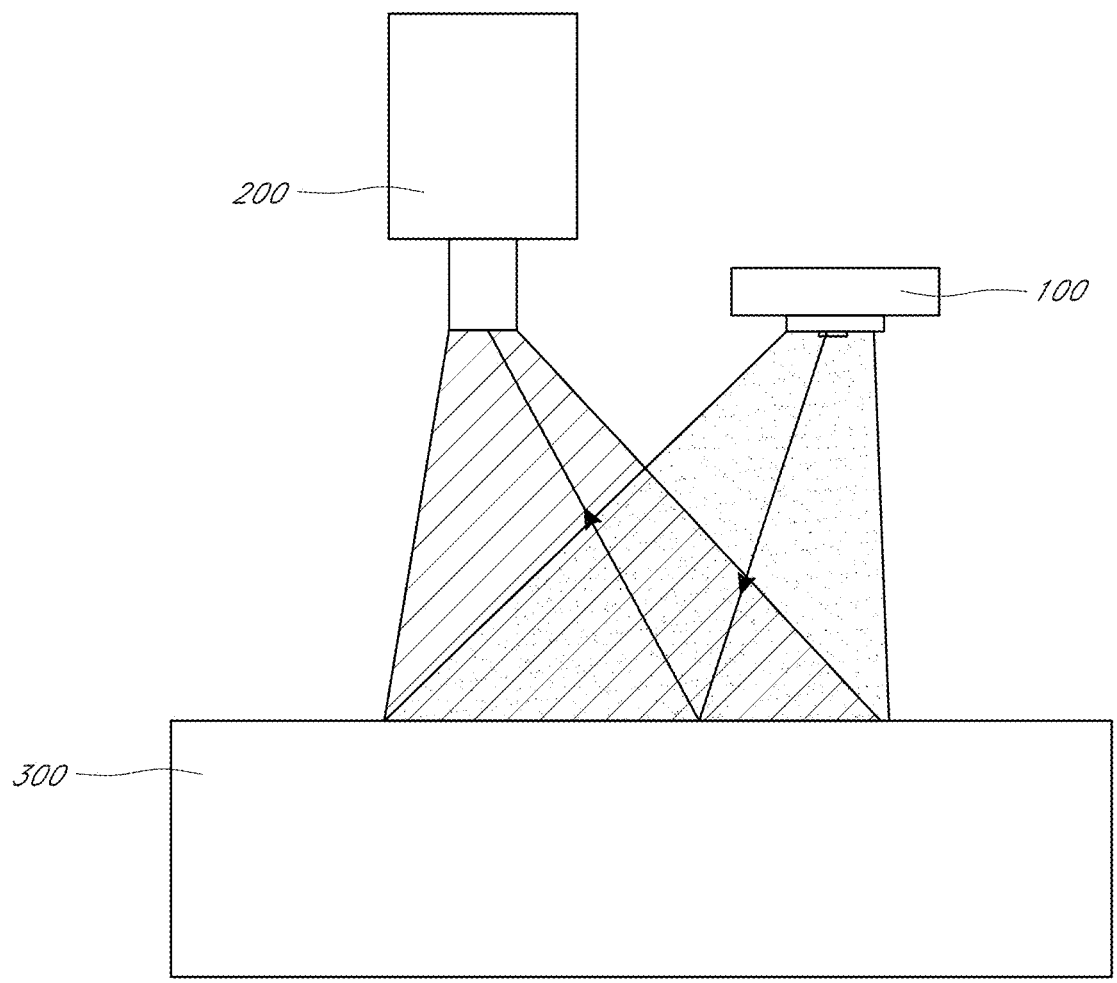
FIGS. 1A-1D schematically illustrate various system configurations.
Figure 1B:
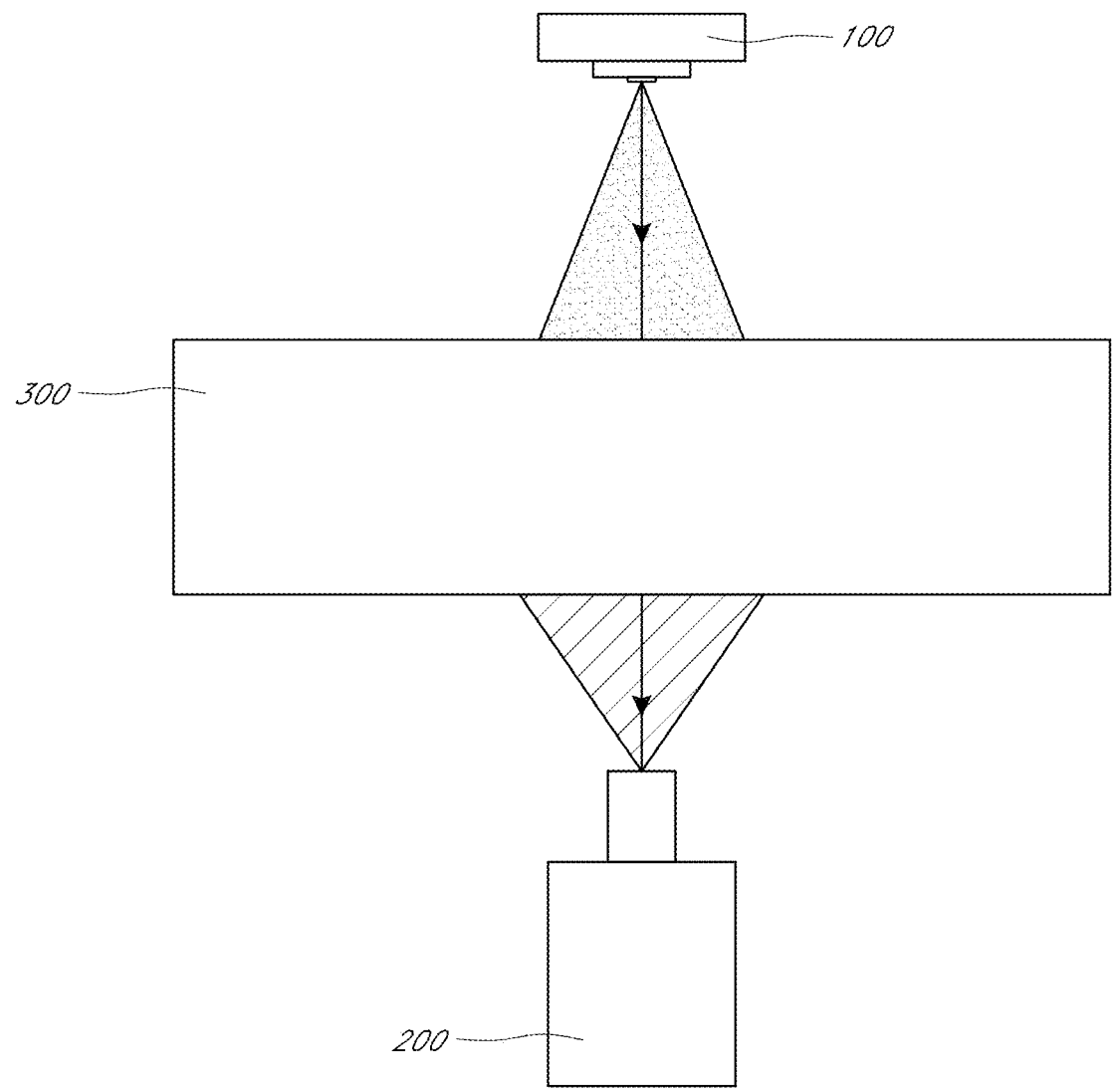
Figure 1C:
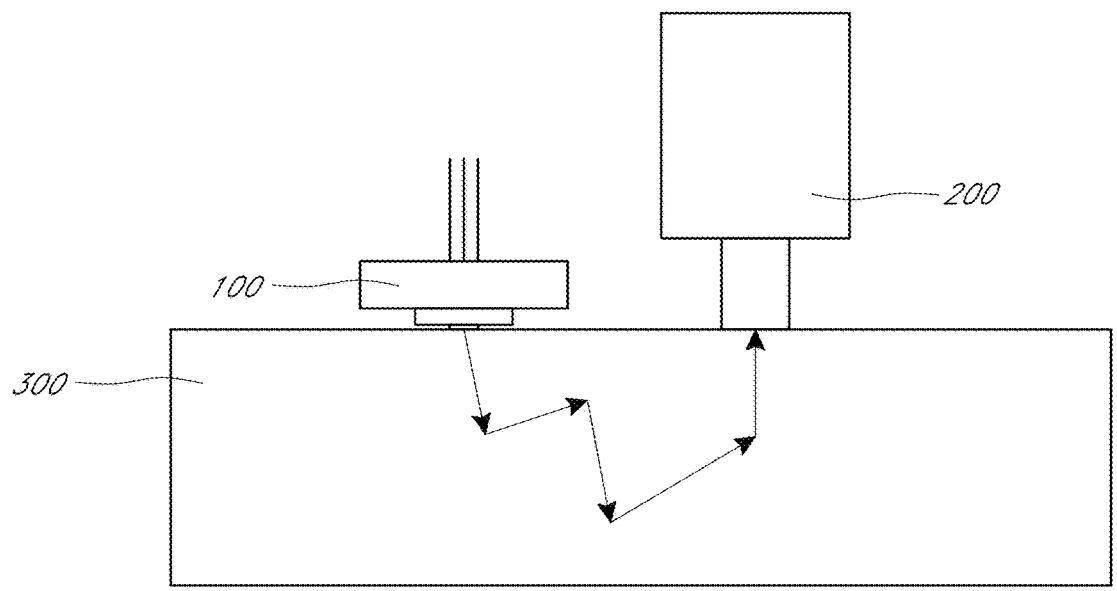
Figure 1D:
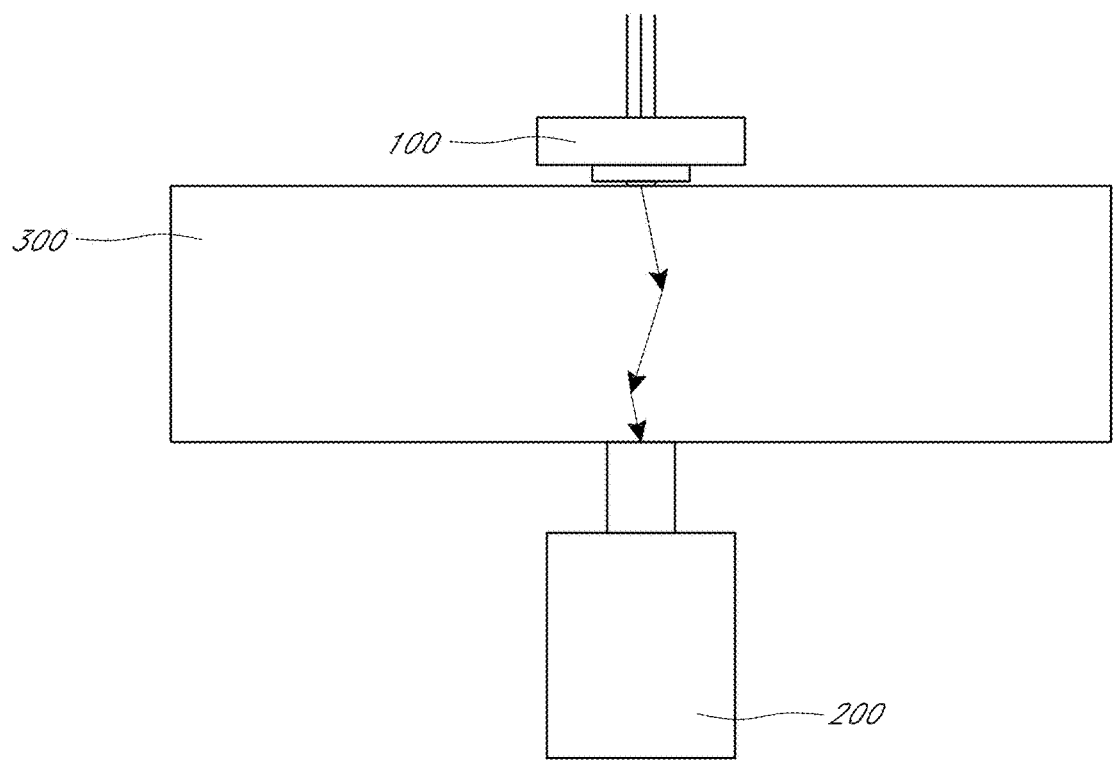

The light source 100 and photodetector 200 may be positionable in any number of configurations relative to the sample 300 including but not limited to being placed in contact or noncontact geometries, or in reflectance or transmission geometries, as seen in FIGS. 1A-1D. The devices are positionable in that they can each be maintained in a relatively constant spatial orientation relative to the sample 300 during the measurement so that changes in the detected signal resulting from movement of the light source 100, photodetector 200, and/or sample 300 relative to one another are negligible relative to the informational content attained from the sample 300. The positionable devices may be affixed to each other, part of an integral device, or distinct structures. One or both of the devices may be removably attached to the sample, such as affixed to a surface of the sample, or they may be free-standing or affixed to a structure independent of the sample 300. At least a portion of the light emitted from a positionable light source 100 is able to reach a surface of the sample 300 and at least a portion of the light detected by a positionable photodetector 200 has contacted the sample 300. FIG. 1A shows a non-contact reflectance geometry wherein the light source 100 and photodetector 200 are both positioned on the same side of the sample 300, neither of which is in direct physical contact with a surface of the sample 300. FIG. 1B shows a non-contact transmission geometry wherein the light source 100 and the photodetector 200 are positioned on opposite sides of the sample 300 through which the light emitted from the light source 100 passes through and in which neither the light source 100 nor the photodetector 200 are in direct physical contact with a surface of the sample 300. The light source 100 and photodetector 200 may or may not be positioned directly across from each other in a transmission geometry. FIG. 1C shows a contact reflectance geometry wherein the light source 100 and the photodetector 200 are both positioned on the same side of the sample 300, both of which are in direct physical contact with a surface of the sample 300. FIG. 1D shows a contact transmission geometry wherein the light source 100 and photodetector 200 are positioned on opposite sides of the sample 300 through which the light emitted from the light source 100 passes through and in which both the light source 100 and the photodetector 200 are in direct physical contact with a surface of the sample 300. Variations are also possible for each geometry wherein one of the light source 100 and the photodetector 200 is in direct physical contact with a surface of the sample 300 and the other is not. These geometries as described and illustrated in FIGS. 1A-1D are non-limiting examples and the systems and methods disclosed herein may be practiced with any suitable configuration of the system components.

During many embodiments, coherent light or at least partially coherent light is emitted by the light source 100 and directed toward the sample 300. The photodetector 200 is positioned to recover at least some of the light emitted by the light source 100 after it has interacted with the sample 300. The light emitted by the light source 100 may be emitted at a constant intensity over a time sufficient for detection. In other embodiments, the light may be emitted according to dynamic patterns. In many embodiments, the light may be emitted and detected over a period of time sufficient to detect changes which occur in the sample 300 and which alter the path of the emitted light and/or properties of the detected light. The processor 500 may be used to record the signal(s) detected by the photodetector 200 over time and/or analyze the signals and/or the temporal changes in the signals over time to determine physiological information about the sample 300.

Figure 2:
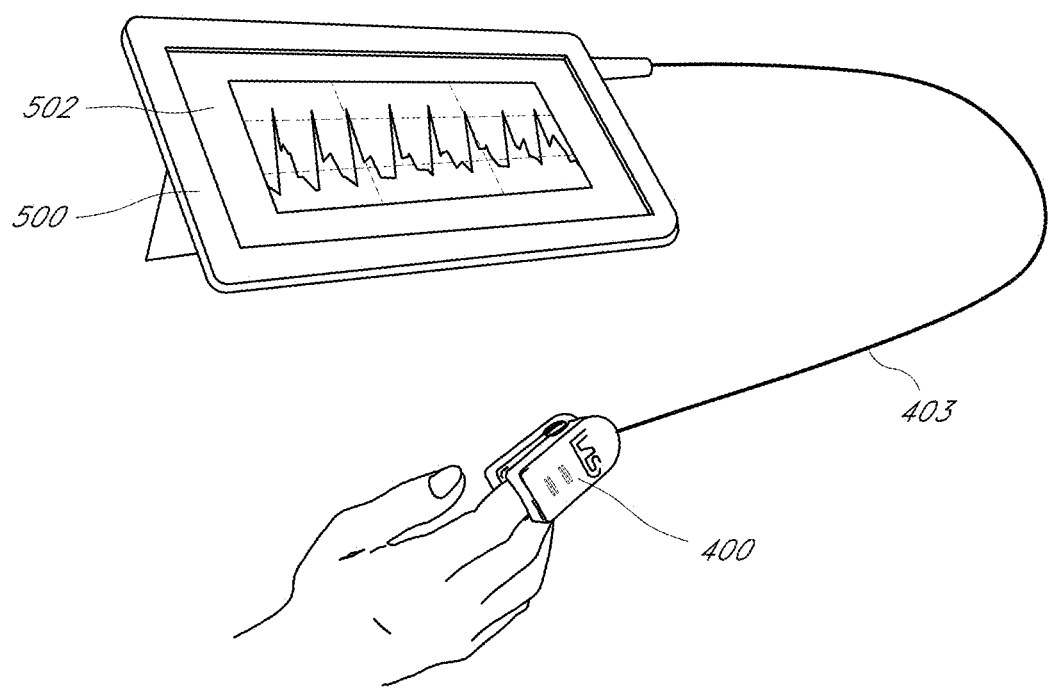
FIG. 2 illustrates an example of an interrogation device coupled to a processor.

FIG. 2 illustrates an example of an interrogation device 400 operatively coupled to a processor 500. The interrogation device 400 can include the light source 100 and photodetector 200 in an integrated or joinable housing. As shown in FIG. 2, the interrogation device 400 may comprise a finger clip for interrogating blood flow within the digit of a subject. The finger clip 400 may be configured to operate in any configuration (e.g., transmission or reflectance as well as contact or non-contact). Some embodiments of the interrogation device 400 may be configured to be wearable or attachable to a subject. These may include, but are not limited to, belts, wrist-bands, skin patches, ear-clips, etc. The interrogation device 400 may be operatively coupled to the processor 500 by a data cable 402, which may transfer data and/or power between the interrogation device 400 and the processor 500. The data cable 402 may be a USB cable or any other suitable cable. In some embodiments, the interrogation device 400 may include wireless functionality for operatively coupling to the processor 500. The processor 500 can include a display 502 for displaying data, such as a detected waveform, an image of a spectral pattern, a histogram of data, etc.

Figure 3:
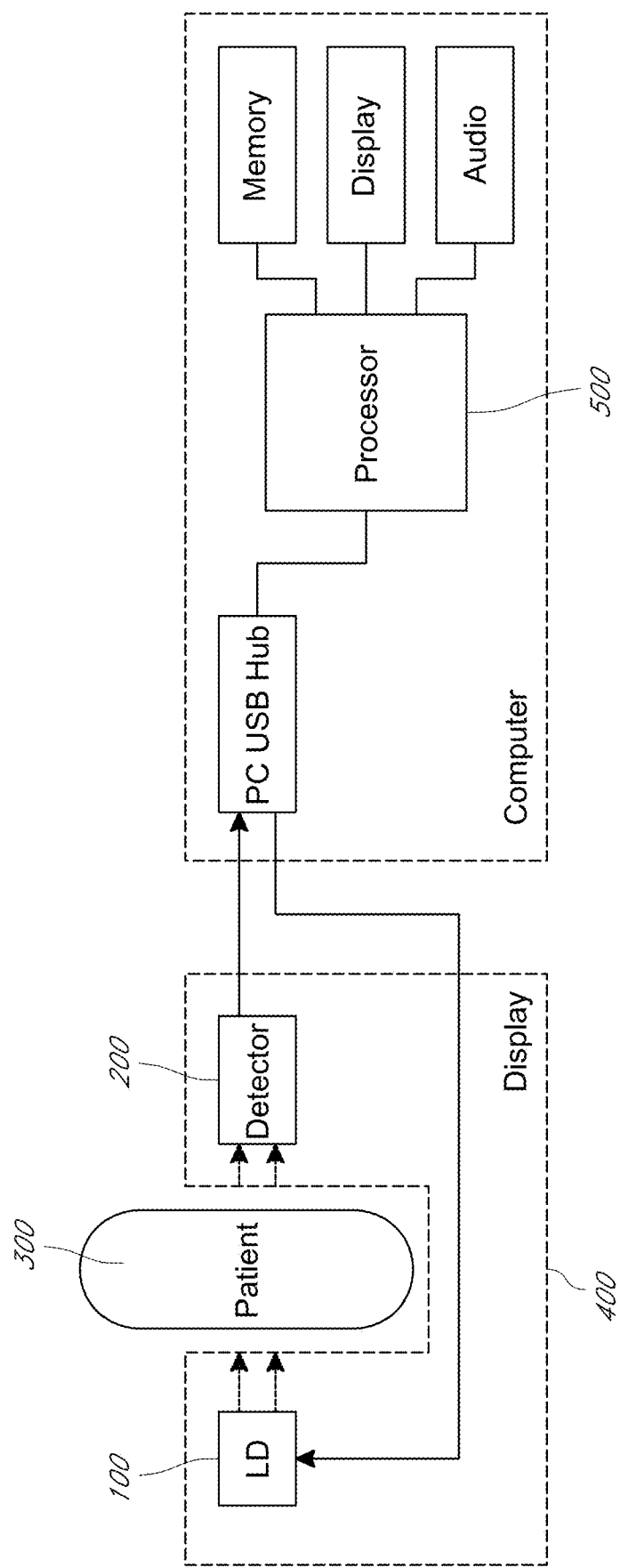
FIG. 3 schematically illustrates the components of a system including an interrogation device coupled to a computer.

FIG. 3 schematically illustrates the interaction of the components of an example interrogation device 400 and a computer. The processor 500 can be part of a computer, a tablet, or any other suitable device. The computer may further include a memory, a display, audio devices, and/or other components. The computer may comprise a PC USB hub for operatively coupling to the interrogation device 400. In some embodiments, a display 502 may be separate from the processor 500. In some embodiments, the interrogation device 400 can include a display. The interrogation device 400 can include the light source 100 (e.g., a laser diode) and/or the photodetector 200. In the example shown in FIG. 3, the light source 100 and the photodetector 200 are configured in a transmission geometry around a sample 300 of physiological tissue. The processor 500 may both exchange information with the photodetector 200, such as receive generated signals, and the light source 100, such as send instructions for controlling operation of the light source 100. In some embodiments, the systems may incorporate feedback for modulating the emission of light from the light source 100 and/or the detection of light by the photodetector 200 according to an analysis of the detected light and/or generated signals by the processor 500.

Figure 4:
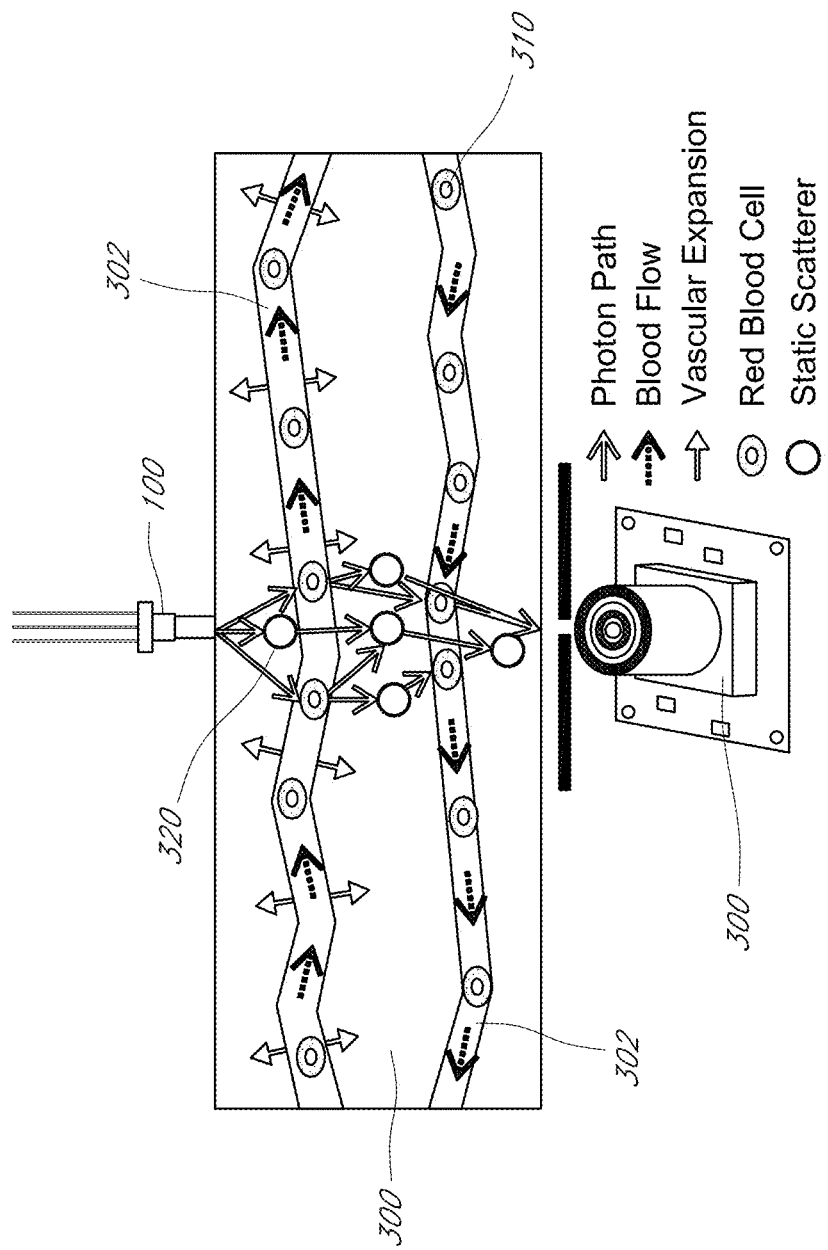
FIG. 4 schematically illustrates the interrogation of vascularized tissue comprising flowing red blood cells.

FIG. 4 schematically depicts the interrogation of a physiological sample 300 which comprises vascularized tissue, according to an embodiment of the invention. In some embodiments, including those related to the interrogation of physiological tissue, the light emitted from the light source 100 passes through a turbid medium in which the light is scattered one or more times, causing the light to diffuse. Within the path of the diffuse light as it travels through the turbid biological medium, there may be vessels 302 of many types. The dotted arrows in FIG. 4 indicate the direction of blood flow. The solid arrows in FIG. 4 represent the vascular expansion of the vessels 302. The vessels 302 may contain light scattering particles (i.e. light scatterers) undergoing motion, such as a steady or pulsatile flow. For example, the red blood cells 310 flowing through blood vessels can scatter and/or absorb the light emitted by the light source 100. Static scatterers 320 may also scatter light emitted by the light source 100. Light traveling through the turbid medium therefore may interact with the both the static base tissue in addition to the flowing blood, as illustrated in FIG. 4.

The flowing blood may impart two major changes on the photons travelling through the sample 300. First, hemoglobin contained within the red blood cells 310 is highly absorptive at a range of useable wavelengths which can be suitably emitted from the light source 100, and acts to attenuate the intensity of the light. Second, the flowing scatterers cause decorrelation of the coherent light emitted by the light source 100. The photodetector 200 is positioned relative to the light source 100 and sample 300 such that at least some of the light emitted by the light source 100 is recovered by the photodetector 200 after diffusing through the sample 300. The photodetector 200 can measure the intensity of the detected light at each of its one or more pixels. The processor 500 operatively coupled to the photodetector 200 may be used to measure the attenuation and the decorrelation of the light traveling from the light source 100 to the photodetector 200. By performing the detection over a period of time sufficient to capture a subject's heartbeat (e.g., one or more cardiac cycles), pulsatile changes in the attenuation or the decorrelation of scattered light associated with the subject's heartbeat may also be measured.

The pulsatile nature of blood pressure and cardiac output imparted by the beating heart causes there to be pulsatility in the net attenuation and decorrelation of coherent light passing through the tissue. The pulsatile attenuation of the light is hypothesized to represent increases in vessel diameter due to increased pressure. The change in red blood cell volume as a result of the pulsatile pressure in the blood vessels may modulate the absorption of light by the red blood cells. This is the source of the Photoplethysmogram (PPG) signal, typically defined as $C*Ln(1/I)$ where I is intensity, Ln is the natural logarithm and C is a multiplicative coefficient used to account for path-length and the molar extinction coefficient of blood. The PPG signal, however, can be calculated in many other ways and embodiments of the invention may use any suitable derivation of the PPG signal.

In addition to the PPG signal, the heartbeat also produces pulsatile fluctuations in blood flow velocity that modulate the correlation of coherent light passing through the interrogated tissue. The scattering of coherent light causes mutual interference in the light waves which randomly alters the intensity (i.e. the amplitude) of the scattered light and may result in observable spatial patterns (i.e. speckle patterns) in the intensity of scattered light, such as the light detected by the photodetector 200. When the coherent light is scattered by moving light scatterers, such as the red blood cells 310 undergoing pulsatile flow, the intensity of observed light at any given point (e.g., at a pixel of the photodetector 200) may change over time as a result of the changing position of the moving light scatterers. The faster the moving light scatterer moves, the quicker the intensity pattern changes and the quicker the coherent light decorrelates. The decorrelation may be observed both spatially and temporally. Because the photodetector 200 cumulates light at each pixel over a finite exposure time (i.e. shutter speed), the changes in intensity that occur during that time, such as the result of the moving scatterers, will blur the detected image. The blurring is analogous to the way in which a fast moving racecar may appear blurry when captured by a slow-speed camera whereas a slower moving pedestrian may appear perfectly clear when captured by the same camera. Similarly, faster moving light scatterers will reduce the spatial contrast in an image detected by the photodetector 200, more than slower moving light scatterers. The exposure time of the photodetector 200 may affect the amount of blurring (i.e. reduction in contrast) observed.

Faster moving light scatterers will also tend to cause more rapid fluctuations at a given point in space, such as at a single pixel, over time. The temporal effects of moving light scatterers may therefore also be observable at individual pixels over periods of time longer than the exposure time. During such time frames, faster moving light scatterers will cause more rapid fluctuations in the detected intensity of a single pixel than will slower moving light scatterers. Therefore, in some embodiments, the systems and methods may comprise a photodetector 200 with a single pixel or single operative pixel. In photodetectors 200 with multiple operative pixels, it may be possible to attain multiple measures of decorrelation over the same time period from multiple individual pixels or from multiple groups of pixels.

The correlation of the scattered coherent light emitted from the light source 100 can be measured with the photodetector 200 and extrapolated to blood flow in a number of ways. The processor 500 may be configured according to a programmed algorithm to derive a contrast metric based on the intensity of light detected by the photodetector 200 at one or more pixels at one point in time or over a period of time. A contrast metric may comprise any suitable quantification of the decorrelation in the intensity of detected light caused by the motion of moving light scatters within the sample 300. One example of a contrast metric is the speckle contrast, defined as sigma/<I> where sigma is the standard deviation of the raw signal and <I> is the average intensity. The standard deviation, sigma, and average intensity, <I>, may be calculated from a sample of pixels belonging to the photodetector 200 according to standard mathematical calculations. The sample of pixels may be a generally contiguous arrangement of adjacent pixels. A pixel may be adjacent another pixel if it shares a common border portion, including an edge or a corner. The sample of pixels may be of any suitable shape and/or size for deriving the contrast metric. A size and/or shape of a sample of pixels may be suitable (e.g. large enough) for a particular sample 300 or type of sample if a broad enough range of contrast is observable over the sample of pixels, such that the contrast may be quantifiably correlated to measures of the moving light scatterers' motion with desirable precision.

Other suitable contrast metrics may be employed by the systems and methods disclosed herein, including the speckle flow index (defined as $1/K^2$ where K is the speckle contrast as described herein), the mean percent difference between pixels of the photodetector 200, the magnitude of fluctuation in the pixel intensities over time, reduction of the pixels to local binary patterns or local ternary patterns, etc. An autocorrelation performed on the signal generated by a single pixel over a period of time may quantify the temporal decorrelation in detected light intensity as a result of the motion of the moving light scatterers.

The calculated speckle contrast relates, at least in part, to the velocity of the moving light scatterers and may be correlated to a flow rate of such light scatterers. The flow rate may be determinable through calibration of a given system in a particular configuration with samples of known flow rates. The flow rate may be a measure of the volume of fluid (e.g., blood) transported per unit of time (i.e. volumetric flow) and may be represented in any suitable units (e.g., $m^3/s$). In some embodiments, the flow rate may be determined as the velocity, or average velocity (e.g., m/s), of the moving light scatterers within a sample 300. In some embodiments, the flow rate may be determined as a measure of volumetric flux (e.g., $m^3 \cdot s^{-1} m^{-2}$) through the blood vessel(s).

When measured rapidly over time, periodic fluctuations in the flow rate may be observed which reveal the heartbeat (i.e. the cardiac cycle). Despite the specific process or formulation, the measurement of a speckle signal generated by the flow of light scatterers (a speckle flow signal) may be derived from sampling the correlation of the coherent light emitted by the light source 100 and detected by the photodetector 200. The systems and methods disclosed herein may use any form of this speckle correlation signal, which may be used to interrogate blood flow and the pulsatility therein, and will be referred to herein as the Speckleplethysmogram (SPG).

Embodiments of the invention comprise systems and methods to produce and analyze a waveform associated with blood flow (SPG) and vessel volume (PPG) during the pulsatile cardiac cycle. The waveforms may be derived by the processor 500 from the signals generated by the photodetector 200, and/or in some embodiments another detector, and may comprise a single determinable value for every sampled point of time across a continuous sample of time. When values for adjacent time points of a waveform are connected, a smooth, continuous, and substantially periodic curve pattern is formed. The waveform may comprise a period, the interval of time that elapses during a single cycle of the waveform before it repeats itself, and a corresponding fundamental frequency—the number of cycles that occur over a unit time (e.g., $s^{-1}$ or Hz). A single cycle of the waveform may be considered a pulse. The SPG signal may be analyzed independently or may be compared to the PPG signal, and then related to a physiological parameter. The systems of some embodiments may comprise the coherent light source 100 which is configured to illuminate a turbid sample, the photodetector 200 which is configured to record the remitted speckle pattern, and/or a processor 500 for analyzing the detected signal(s) and generating physiological relevant data. The speckle pattern may be used to determine blood flow and blood volume during the pulsatile cardiac cycle of an interrogated subject, which produces the SPG and PPG waveforms. The two distinct signals—derived from the coherent light of a single light source 100—may be acquired, processed and analyzed to provide information related to the physiology and pathology of the subject.

In some embodiments, relevant physiological information may be obtained directly from the signals. A signal may be decomposed into one or more of its characteristic features, which may be identified and extracted from the signal by the processor. Physiological parameters may be determinable by comparing characteristic features of a waveform to characteristic features of the same waveform or another waveform. Various features of the signals may comprise embedded information descriptive of physiological parameters. A characteristic feature may comprise any determinable characteristic of the signal which is related to or descriptive of some physiological information. These may include, but are not limited to, the timing of peaks or other discernible shapes that are repetitive in the waveform, magnitudes of slopes (e.g. of a peak), peak sharpness (e.g. width or height-to-width ratio), amplitudes of peaks, differences in amplitudes between peaks, etc. Both pulsatile and non-pulsatile amplitudes of the waveforms can provide useful physiological information. Pulsatile amplitudes can include any part of the waveform feature that originates from the cardiac pulse, while non-pulsatile amplitudes may characterize effects that do not originate in the cardiac pulse (e.g., motion of the patient, ambient light interference, etc.). For example, a non-pulsatile amplitude may characterize the flow amplitude after purposefully obstructing the pulse through arterial occlusion (e.g., via an inflatable arm cuff).

Comparisons of features can include, but are not limited to, comparisons of quantifiable values and the relative timing of features. Comparisons may be quantitative or qualitative. Quantitative comparisons may include, for example, the difference or ratio between the magnitudes of features (e.g., peak amplitudes) or the timing of features (e.g., a time delay). Qualititatve comparisons may include a determination of which feature has a greater or lesser quantified value, which waveform has more or fewer of a feature or type of feature, or which feature occurred earlier or later in time. For example, a characteristic feature may be the number of occurrences of local extrema or the timing occurrences of local extrema. The local extrema may comprise time points in which the waveform experiences a relative maximum or minimum value over a period of time. The local extrema may include any point where the derivative changes from positive to negative or vice-versa and is therefore zero (as best determinable by the processor 500). The processor 500 may count the number of occurrences of a maxima, minima, or both within one or more pulses of a waveform, which may be indicative of pulsatility of the waveform. The processor 500 can also determine the timing of the extrema, which may be used to determine time delays within the signal or between two signals.

In some embodiments, the methods of analyzing the waveforms generated by the photodetector 200 and/or other detectors comprises a decomposition of the one or more of the waveforms into basis functions and respective amplitudes. Each basis function may comprise a mathematical expression relating a dependent variable to an independent variable. The dependent variables for each basis function may be scaled (i.e. multiplied) by a single coefficient (i.e. respective amplitude) so that a linear combination or superimposition of the basis functions scaled by their respective amplitudes approximates the waveform or a representation of the waveform over a range of the independent variable. The basis functions may be any generalized basis functions. Physiological parameters may be determinable by comparing the amplitudes of the basis functions. Comparisons may include, but are not limited to a determination of which basis function has the greater/lesser amplitude, the difference in amplitudes, and/or the ratio of one amplitude to another.

In some embodiments, the basis functions may be selected so that the decomposition results in a signal that is dependent on an independent variable other than time. For example, the decomposition may transform the waveform from being a time-dependent function into a frequency-dependent function, which can be described by the superimposition of scaled frequency-dependent basis functions (i.e. a time-frequency transformation). In such a manner, the decomposition may be equivalent to performing a Fourier transform on the time-dependent waveform. In many embodiment methods, the basis functions may be periodic (e.g. sinusoidal) and the frequencies of each basis function may be integer multiples of a fundamental frequency of the waveform (i.e. harmonics). The first harmonic can be defined as equivalent to the fundamental frequency. The waveforms may be decomposed into basis functions that define other spaces as well (i.e., defined by independent variables other than time or frequency).

In some embodiments, the methods of analysis comprise various steps for analyzing the decomposed SPG signal alone to recover a physiological parameter. In other embodiments, the methods of analysis comprise steps for comparing the SPG signal to a second signal, wherein the second signal is of a physiological origin distinct from that of the contrast metric (i.e. the speckle flow signal). For example, the second signal may relate to a metric of photo-intensity, rather than a metric of contrast, such as the PPG signal, which originates in the periodic volumetric expansion of the vasculature, rather than the periodic change in flow rate. The detected photo-intensity metric may be converted into a metric of absorption. This conversion may be performed numerically using the radiative transport equation or estimated through one of various diffusion approximations. For example, the metric of absorption may be approximated by using the Beer-Lambert law with a-priori estimate for mean path-length. The Beer-Lambert law states that the percent of intensity transmitting through a sample is inversely related to the exponential of absorption coefficient times the path length. The metric of absorption can also be approximated by the inverse intensity of the detected signal.

The second signal may originate from any reference signal including but not limited to an ECG signal, PPG signal, a blood pressure signal, other measures of cardiac output, etc. In some embodiments, the ECG signal or other reference signal may be used in the absence of, or as a substitute for the PPG signal. The SPG signal and reference signal may each be thought of as modified carrier waves, wherein the carrier wave is a simple waveform (e.g. a sinusoidal waveform) representing the periodicity of the cardiac cycle and the modifications of the carrier wave comprise embedded physiological information. In some embodiments the reference signal may not be a waveform. For example, the reference signal may be a single value, a collection of intermittently sampled values, or an average value over a continuous sampling period (e.g., blood pressure readings).

Some features may be intrinsic to the dynamics of each signal alone and other features may relate to a comparison of the signals. Features that are intrinsic to each signal may be described by the amplitudes of selected basis functions or by the ratios of the amplitudes (i.e. coefficients) of selected basis functions. In the case of frequency-dependent basis functions, the ratios may be harmonic ratios. The ratios may be calculated by dividing the resolved amplitude of one basis function by the resolved amplitude of another basis function. In some embodiments, one or more ratios are calculated for each pulse (i.e. cycle) in the recorded waveform over a sample period of time (e.g., 100 pulses, 500 pulses, 1000 pulses, 5,000 pulses, 10,000 pulses, etc.). The ratios may be simple or complex and may include sums, differences, products, and quotients of amplitudes or other suitable mathematical operations. The variability across the distribution of pulses may relate to a physiological parameter. The method of analysis may comprise determining a distribution of ratio values for the sample of pulses. In doing so, the processor 500 may generate a histogram, in which a continuous range of ratio values are discretized and the number of sampled pulses exhibiting a ratio value that falls within each discretized range are tabulated (a graphical representation of the histogram does not necessarily need to be displayed).

Figure 5:
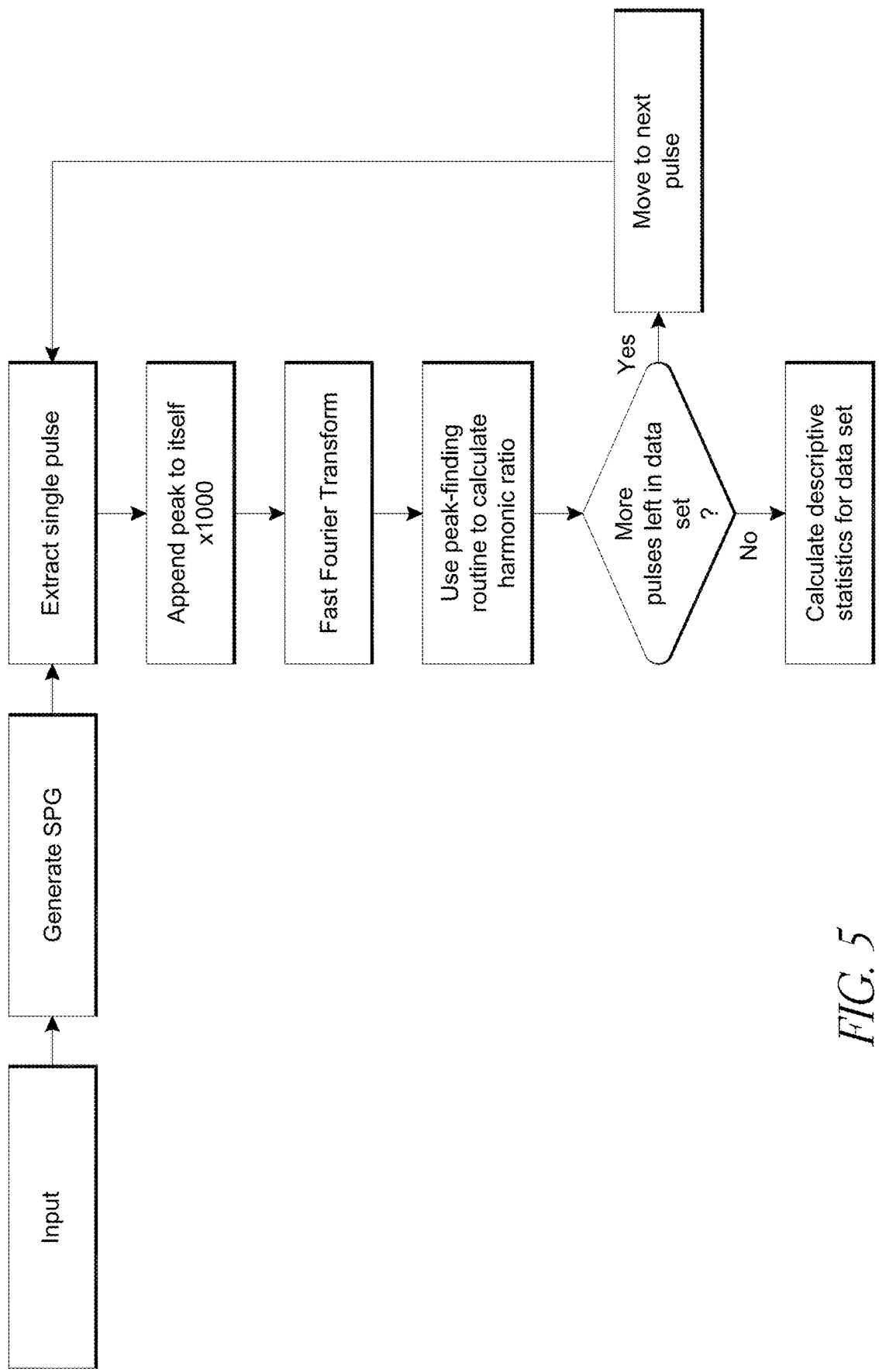
FIG. 5 schematically illustrates an example of an algorithm for calculating descriptive statistics from an SPG signal.

FIG. 5 illustrates an example of an algorithm that may be performed by the processor 500 to calculate descriptive statistics on an SPG signal generated by the processor 500 from input received from the photodetector 200. The algorithm instructs the processor 500 to extract single pulses from the SPG signal, append the extracted pulse to itself 1000 times, perform a Fast Fourier Transform (FFT), use a peak-finding routine to calculate a harmonic ratio, and repeat the process for each sequential pulse identified in the data set derived from the SPG signal. Once every pulse is completed, the processor 500 may generate statistics describing the distribution of calculated harmonic ratios within the data set.

Features that take into account both signals include, but are not limited to: timing differences between distinct features in PPG signal and SPG signal (e.g., the signal peak, systolic peak, diastolic peak, dicrotic notch, the minimum (i.e. "foot"), etc.), differences between the full-width-half-maxima, differences between slopes, differences between peak sharpness, the phase difference of the carrier wave, and the relative magnitudes (i.e. amplitudes) of carrier wave harmonics. For example, one or more harmonic ratios of the SPG signal may be compared to the same harmonic ratios in the reference signal (e.g. a ratio of ratios). The harmonic ratios can characterize the pulsatility of a signal (i.e. larger harmonic ratios characterize more pulsatile signals) and the comparison of the harmonic ratios may be indicative of tissue health. For instance, someone with advanced vessel disease may display a relatively pulsatile SPG signal and a relatively weak PPG signal, with much smaller harmonic ratios. For example, the ratio of the $3^{rd}$ harmonic to the $5^{th}$ harmonic may be used to characterize pulsatility. The methods may comprise any useful comparison of the SPG signal to a reference signal for extracting the timings of features and/or comparing features, which are descriptive of physiological parameters. The embodiments disclosed herein generally relate to the structure and timing features of the SPG signal. These timing features can be derived from one of several technologies including but not limited to PPG or ECG.

Figure 6:
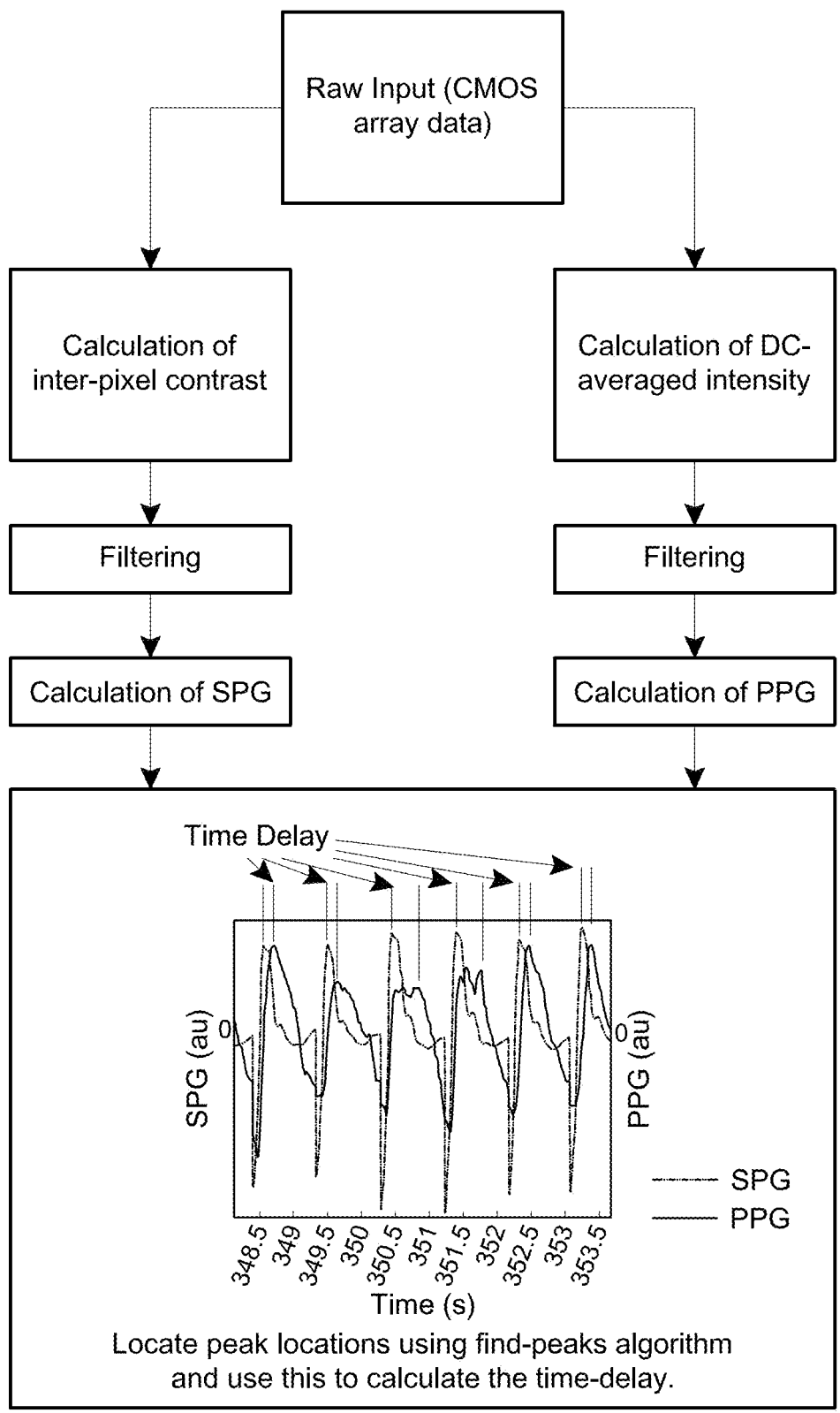
FIG. 6 schematically illustrates an example of an algorithm for calculating the time delay between an SPG and a PPG signal.

FIG. 6 illustrates an example of an algorithm that may be performed by the processor 500 to calculate the time delay between a detected SPG signal and a detected PPG signal. The processor 500 may generate the SPG signal and the PPG signal from the same raw input signal received from the photodetector 200. The SPG signal can be generated by calculating a measure of inter-pixel contrast in the raw signal detected by the photodetector 200. The PPG signal can be generated by calculating the DC-averaged intensity of the raw signal detected by the photodetector 200. Both signals may be additionally filtered by the processor 500. The processor 500 may employ a peak-finding algorithm to locate peaks within the SPG and PPG signals and calculate a series of time delays between corresponding peaks.

The SPG waveform decomposition method may include but is not limited to: Fourier decomposition to determine harmonic amplitudes, wavelet decomposition, decomposition into non-continuous basis functions (e.g., comb or rectangle functions), and abstract feature decomposition. Abstract feature decomposition decomposes the waveform into abstract features (i.e. one or more non-continuous quantitative values, determinable and comparable by the processor 500, which describe one or more characteristic features of the waveform). Abstract decomposition, for example, can include decomposition of a waveform into characteristic features, including but not limited to, the timing of peaks, a count of the integer number of distinctive peaks within a particular time period, the count of the integer number of times that the waveform breaches a particular amplitude, and/or other characteristic features described herein. In some instances, the features may be a binary description of whether a certain criterion is met (e.g., whether the systolic peak is 50% higher than the diastolic trough).

Figure 7A:
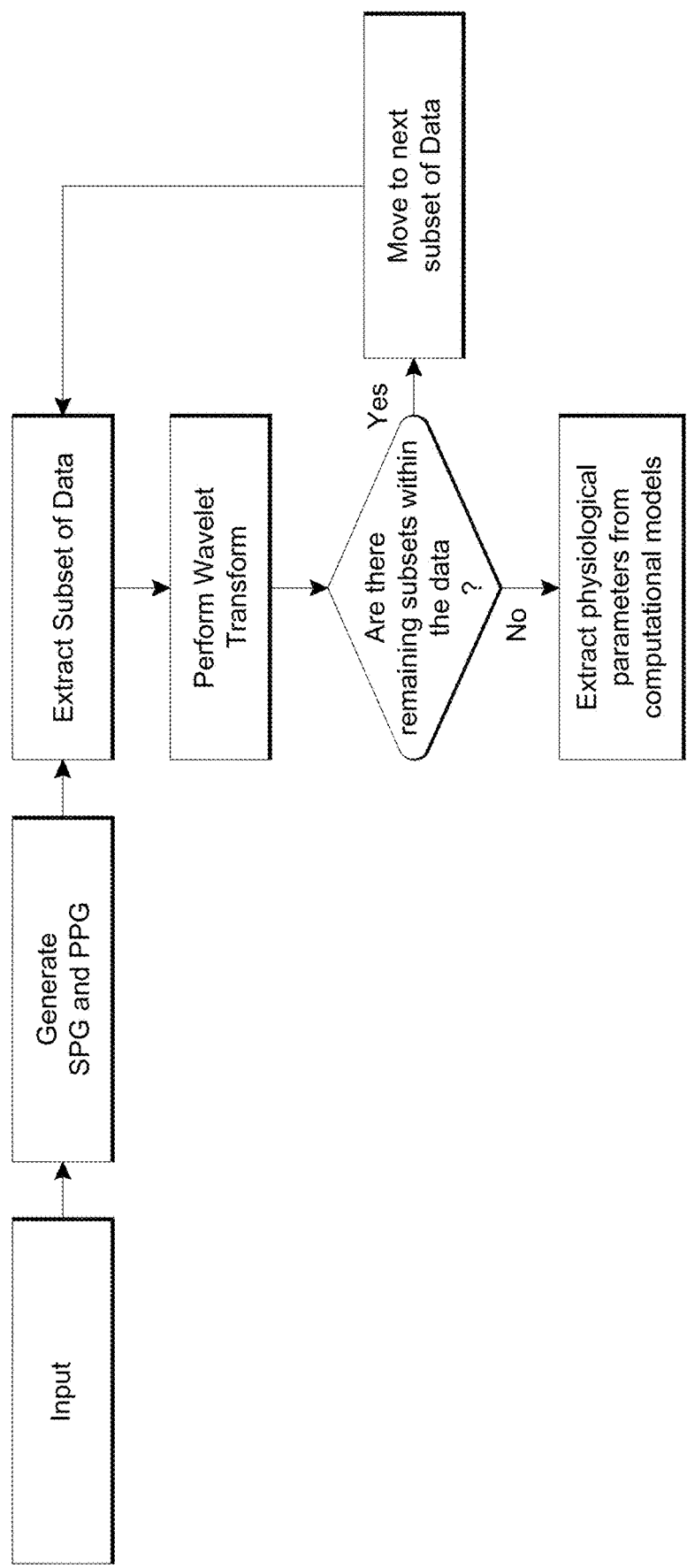
FIGS. 7A-7C illustrate the use of a wavelet transform on SPG signals.
Figures 7B, 7C:
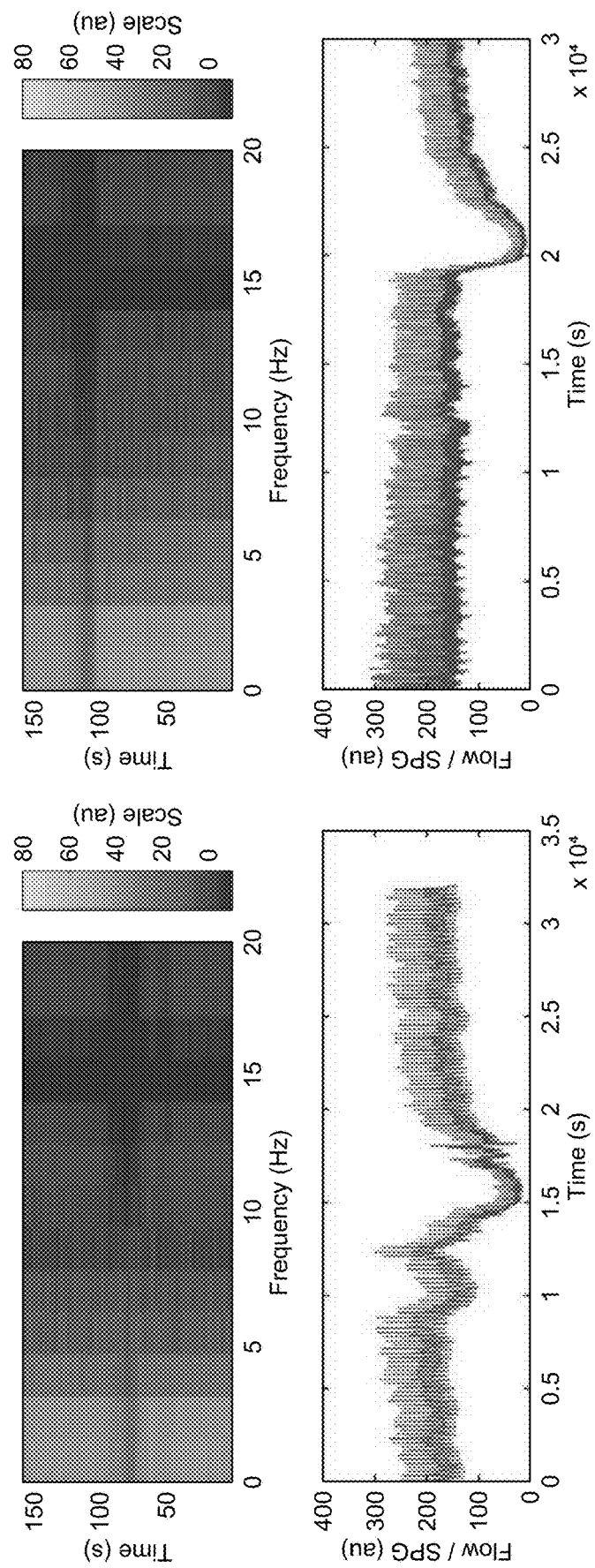

In addition to decomposing waveforms, the processor 500 may generate and/or display useful representations of the data, such as histograms and scalograms. For example, the processor 500 may generate a scalogram as a representation of the amplitudes of a wavelet transform. FIG. 7A illustrates an example of an algorithm that may be performed by the processor 500 to extract physiological parameters from SPG and PPG signals generated from detector 200 input using the processor 500 to perform a wavelet transform on extracted subsets of data from the signals. Wavelet transforms advantageously provide frequency information on all time points, without the need to select a section for analysis (e.g., as with a FFT). FIGS. 7B and 7C illustrate examples of SPG signals (bottom) generated by a processor from detector input and scalograms (top) generated by a processor from the SPG signals. FIG. 7B illustrates baseline data collected on a subject with normal vascular tone. FIG. 7C illustrates data collected from the same subject post-exercise (vasodilation conditions). As shown in FIGS. 7B and 7C, increasing arterial resistance may be correlated with decreased higher frequency arterial components, as indicated by the lower scale values, generally at all sampled time values, for higher frequencies (e.g., 5-6 Hz) in FIG. 7C relative to FIG. 7B.

EXAMPLES

The following are specific examples of the systems and methods presented herein.

Example 1: SPG-PPG Time Delay

The example here demonstrates the extraction the time-delay between the SPG and PPG signals. The SPG signal, which is representative of the blood flow velocity, has slightly different morphological characteristics than the PPG signal, which is representative of the tissue vascular expansion. One contrasting feature between the PPG and SPG signals is that the PPG signal peak (i.e. the maxima within a pulse) lags the SPG peak in time. Different repetitive features in each signal such as the peak or the trough (i.e. the minima within a pulse) can be used to measure this timing offset between the peaks.

Figure 8A:
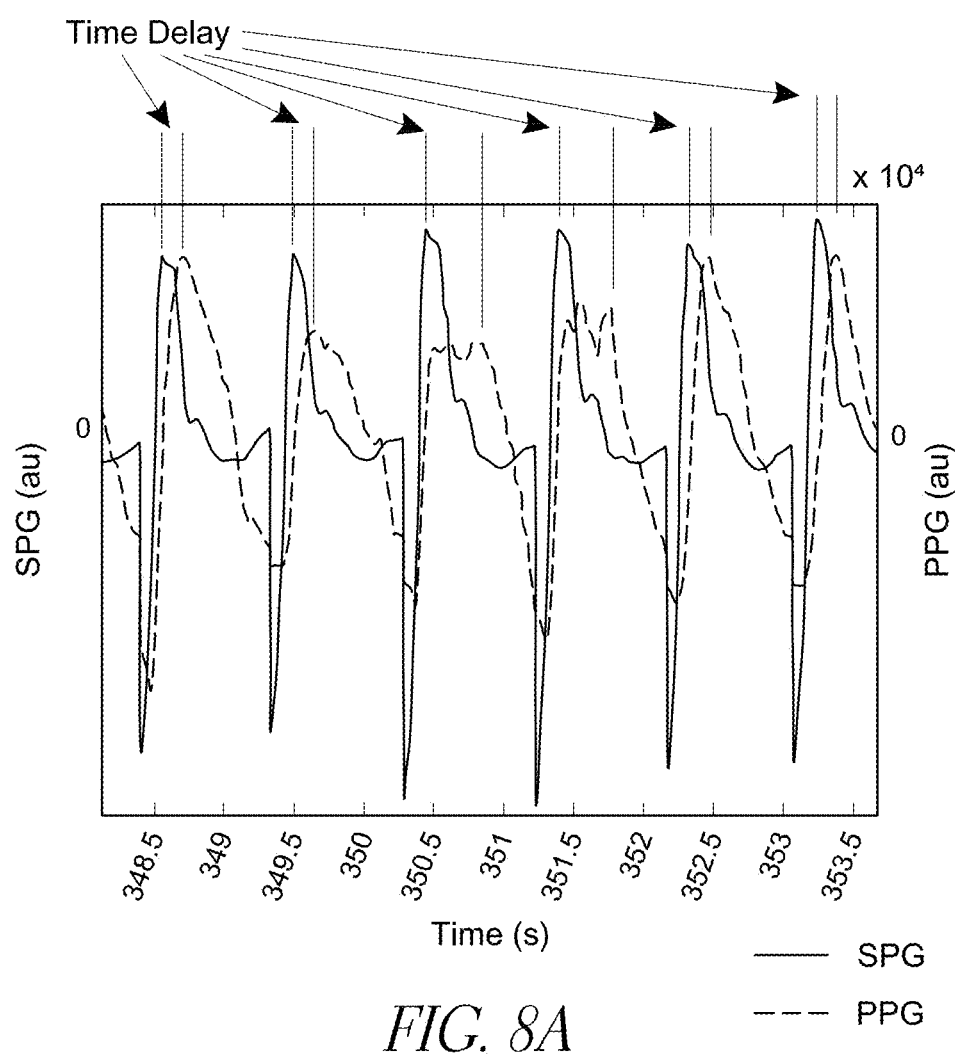
FIGS. 8A-8C depict data obtained by a comparison of PPG and SPG signals.
Figure 8B:
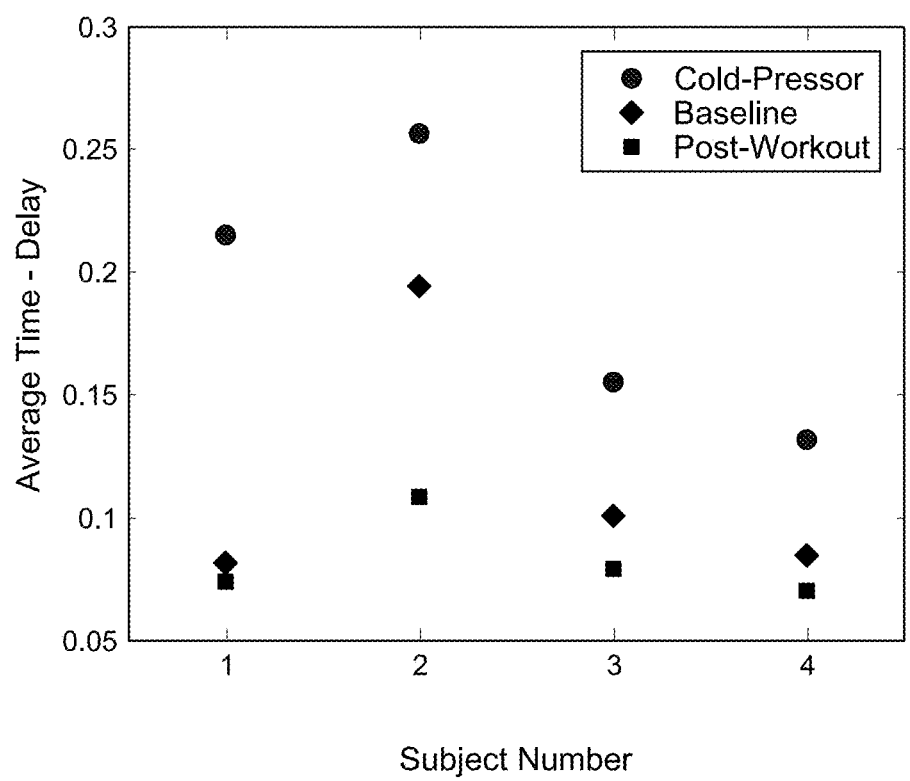
Figure 8C:
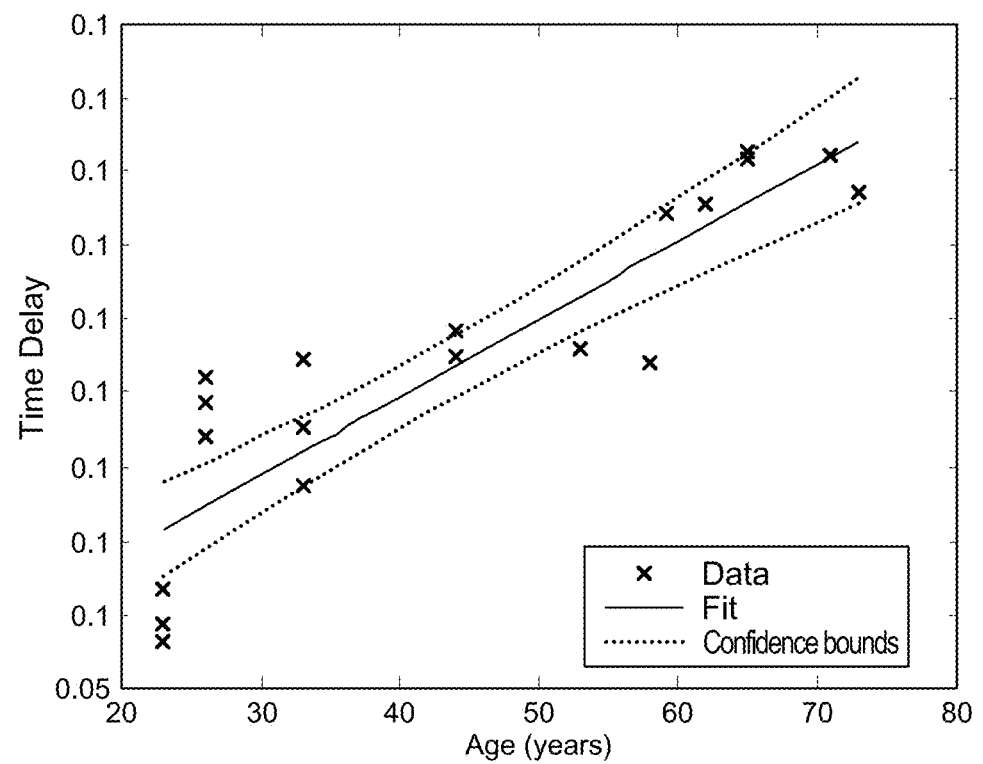

FIG. 8A shows the raw detected SPG and PPG signals in blue and red, respectively, over the same time frame. The slight timing offset between the two signals in this example (indicated by the black lines) is visually discernible. Measurement of the timing offset provides meaningful physiological information. FIG. 8B shows the average time-delay of four subjects in three different physiological conditions. The squares were acquired post-exercise, the diamonds were acquired at a baseline, and the circles were acquired during a cold-pressor challenge (the cold pressor challenge consists of submerging the subject's hand in ice water for around 30 seconds). This data demonstrates that the timing offset features are related to vascular tone. Vascular tone may refer to the degree of constriction experienced by a blood vessel relative to its maximally dilated state. Exercise relaxes vasculature to increase blood flow while the cold-pressor constricts vasculature to reduce blood-flow. The data shows that larger timing offsets are experienced for all subjects when the blood vessels are relatively constricted. The increase in vascular tone (i.e. arterial stiffness) may cause a delayed and/or an attenuated elastic expansion of the vessel. The result can be detected in the timing offset and/or peak sharpness of the detected PPG signal relative to the SPG signal. Finally, FIG. 8C shows the correlation between the average time-delay and subject age. In this study, a baseline signal was recorded and signals were then continually recorded as the subjects underwent arterial occlusion and recovery by applying a blood pressure cuff to the subjects' arms and cyclically pressurizing the cuff (e.g., 100-220 mmHg for no more than 3 minutes) and then quickly depressurizing the cuff (e.g., 3-5 minute recovery). In doing so, the subjects' interrogated blood vessels are expected to cycle between vasoconstrictive and hyperemia-induced dilated conditions. The time delay for each subject in FIG. 8C was averaged during post-hyperemia vasodilation. The data shows that the timing offset tends to increase with age. The r-squared coefficient of this correlation is 0.8 and indicates that time-delay may be a sensitive measurement for atherosclerosis associated with the aging process. Atherosclerosis can reduce blood vessel compliance and, like vascular tone, may delay and/or attenuate the filling of the interrogated blood vessel. Therefore, the measured time delay between the detected PPG signal and SPG signal may be predictive of atherosclerosis.

Example 2: SPG Harmonic Content

This example demonstrates the recovery of physiological information from independent analysis of the dynamics of the SPG signal. As pulsatile flow travels from the heart to the extremities the input impulse is distorted by several vascular characteristics that include the atherosclerotic obstruction, arterial branching, vascular compliance and blood pressure. By analyzing the frequency content of the SPG waveform on a pulse-by-pulse basis it is possible to recover these characteristics quantitatively. FIGS. 9A-9E demonstrates a method for extracting the frequency domain harmonic content from a detected SPG signal. A single pulse is first identified within time-series data by the processor 500 (FIG. 9A), extracted by the processor 500 (FIG. 9B), appended to itself numerous times such as, for example, 1000 times (FIG. 9C), and then frequency transformed via FFT in order to produce a harmonic spectrum that approximates a Fourier Series Expansion (FIG. 9D). This spectrum is then used to calculate a harmonic ratio based off any two harmonics. This process is then repeated for every single pulse within a given data set producing a distribution of harmonic ratios, as illustrated in FIG. 9E. The harmonic ratio may be defined relative to the fundamental frequency (e.g., the second harmonic ratio, Harmonic Ratio 2 (SPGHR2), is the ratio of the second harmonic to the fundamental frequency and so on) or between each other (e.g., Harmonic Ratio 3-2 is the ratio of the third harmonic to the second harmonic and so on).

Figure 10:
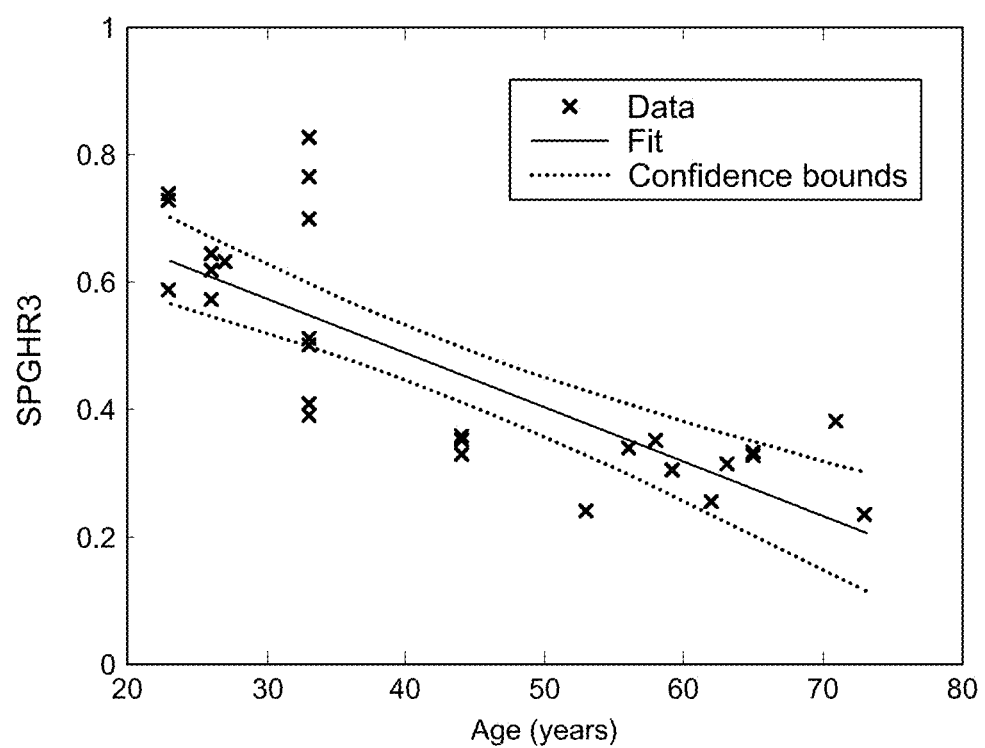
FIG. 10 depicts data showing the correlation between measured harmonic ratio and subject age.

FIG. 10 depicts the correlation between the third harmonic ratio of the SPG signal (SPGHR3) and subject age. It shows a strong inverse correlation between the third harmonic ratio and age, indicating that frequency content, as derived by the disclosed systems and methods herein, decrease as individuals get older. Frequency content (i.e. harmonic content) can generally be described as the frequency components of a waveform. Harmonic content may be correlated with overall vascular health. It has been shown in the literature that the pulsatile frequency content (relatively higher frequencies) decreases with age due to index mismatch at arterial branches that attenuates high frequency signal components. The refractive index between the liquid and vessel influences the propagation of a velocity wave down a vessel and can be affected by the cross-sectional area and elastic composition of an artery. Healthy vasculature is generally well-matched in the refractive indexes between parent and daughter vessels at vessel branching points. Atherosclerosis can affect both the elasticity and cross-sectional area of blood vessels and therefore the refractive index of blood vessels. As the refractive index is dependent on the cross-sectional area of the blood vessels, atherosclerosis can affect the refractive index of larger parent vessels differently from how it affects the refractive indexes of smaller daughter vessels. Atherosclerosis may result in index mismatch between parent vessels and daughter vessels. The systems and methods disclosed herein may be used to quantify harmonic content and/or characterize vascular health of a subject. The determined physiological information may be indicative of index mismatch at sites of arterial branching, which may be predictive of atherosclerosis.

Example 3: Further Evidence of Clinical Utility

Figure 11:
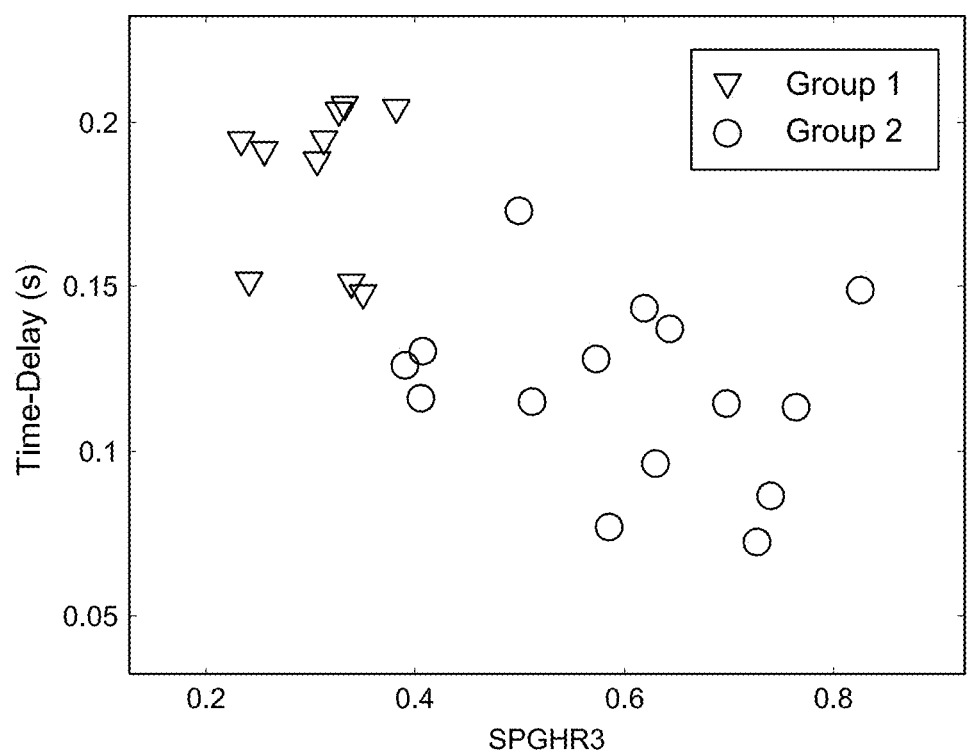
FIG. 11 depicts a scatter plot resolving two groups of subjects with different health statuses based on a measured time delay and harmonic ratio of SPG signals.

Using both the timing comparison between the two signals as well as the frequency content derived from the structure of the SPG, it was possible to separate two distinct patient groups. The first group consisted of individuals aged 50+ who have some combination of cardiovascular risk factors. The second group consisted of healthy controls under the age of 35. FIG. 11 depicts a scatter plot of the subjects (the first group indicated by triangles and the second group indicated by circles) with respect to their timing offset (i.e. time-delay) and their measured third harmonic ratio, as determined by the systems and methods disclosed herein. As shown in FIG. 11, the two groups can be discernably separated within the scatter plot based on the time-delay and the third SPG harmonic ratio. In general, the first group, comprising older subjects with cardiovascular risk factors, tend to have larger timing-offsets and lower third harmonic ratios than the second group, comprising younger healthy subjects, which generally positions the first group in the upper left portion of the scatter plot and the second group in the lower right portion of the scatter plot. The combined timing-delay and third harmonic ratio may therefore be a useful factor (along with age) in diagnosing cardiovascular disease. The systems and methods disclosed herein may have other potential clinical applications as well.

While the present invention has been described in terms of particular embodiments and applications, in both summarized and detailed forms, it is not intended that these descriptions in any way limit its scope to any such embodiments and applications, and it will be understood that many substitutions, changes and variations in the described embodiments, applications and details of the method and system illustrated herein and of their operation can be made by those skilled in the art without departing from the spirit of this invention.

What is claimed is:

1. A system for determining one or more physiological parameters in a subject, the system comprising:
    a. a light source positionable along a first location outside of the subject, and configured to direct light from the first location toward a plurality of particles flowing in pulsatile motion within a blood vessel inside of the subject;
    b. a photo-sensitive detector positionable along a second location outside of the subject, and configured to detect light from the plurality of particles and generate only one raw signal in response to the detected light, wherein the detected light includes the light scattered and absorbed by the plurality of particles; and
    c. a processor comprising a program and a memory, wherein the processor is operably coupled to the photo-sensitive detector and configured to receive and store in memory the raw signal from the photo-sensitive detector generated over a period of time, and wherein the processor is further configured to generate a first waveform and a second, physiologically distinct waveform from the first waveform based on the raw signal; wherein the processor is programmed to:
        i. derive contrast metrics and intensity metrics from the raw signal;
        ii. calculate the first waveform from the contrast metrics and the second waveform from the intensity metrics;
            wherein the first waveform is a speckleplethysmograph (SPG) waveform and the second waveform is a photoplethysmogram (PPG) waveform;
        iii. decompose the first waveform and the second waveform into corresponding one or more characteristic features; and
        iv. make a comparison of the corresponding one or more characteristic features of the first waveform and the second waveform to determine the one or more physiological parameters, wherein the one or more physiological parameters are selected from a group consisting of atherosclerotic obstruction, vascular compliance, blood pressure, cardiac output, venous state, vascular tone, blood flow, hemodynamics, and combinations thereof.

2. The system of claim 1, wherein the processor is further programmed to convert the contrast metrics into metrics of volumetric flow and convert the intensity metrics into metrics of volumetric expansion.

3. The system of claim 1, wherein the one or more characteristic features are amplitudes of a basis function and wherein the processor is further programmed to generate a histogram based on a ratio of basis function amplitudes.

4. The system of claim 1, wherein the one or more characteristic features are amplitudes of a periodic basis function, and the decomposition is equivalent to a time-frequency transform.

5. The system of claim 1, wherein the one or more characteristic features are amplitudes of a wavelet basis function, and the decomposition represent a wavelet transform.

6. The system of claim 1, wherein the one or more characteristic features describe widths of the first waveform and the second waveform.

7. The system of claim 1, wherein the one or more characteristic features are timing occurrences of local extrema of the first waveform and the second waveform, and wherein the processor is further programmed to calculate a time delay between the first waveform and the second waveform based on the timing occurrences of local extrema of the first waveform and the second waveform and further determine the one or more physiological conditions based on the time delay.

8. The system of claim 1, wherein the one or more characteristic features are amplitudes of local extrema of the first waveform and the second waveform, and wherein the processor is further programmed to compare one or more of the amplitudes of the local extrema of the first waveform and the second waveform, a difference in amplitudes of local extrema of the first waveform, and a ratio of amplitudes of local extrema of the first waveform and the second waveform to determine the one or more physiological conditions.

9. The system of claim 1, wherein the one or more characteristic features are magnitudes of sloped of the first waveform and the second waveform, and wherein the processor is further programmed to compare magnitudes of slopes of the first waveform and the second waveform to determine the one or more physiological conditions.

10. A method for determining one or more physiological parameters from particles in pulsatile motion within a physiological system, the method comprising:
   a. positioning a light source at a first site outside of the physiological system;
   b. actuating the light source, such that light is directed toward the particles;
   c. positioning a photo-sensitive detector at a second site outside of the physiological system, wherein the second site is located along a path of light scattered and absorbed by at least some of the particles;
   d. using the photo-sensitive detector to detect light scattered and absorbed by at least some of the particles over a period of time in response to the directed light and generate only one raw signal based on the detected light;
   e. communicating the raw signal related to the detected light to a processor;
   f. calculating a contrast metric from the raw signal and an absorption metric from the raw signals;
   g. producing a first, contrast waveform based on changed in the contrast metric over time due to the pulsatile motion of the particles within the physiological system, wherein the first, contrast waveform is a SPG waveform;
   h. producing a second, absorption waveform based on changes in the absorption metric over the time due to pulsatile expansion of the particles within the physiological system, wherein the second, absorption waveform is a PPG waveform;
   i. decomposing the first, contrast waveform and the second, absorption waveform into respective characteristic features;
   j. making a comparison of the respective characteristic features decomposed from each of the first, contrast waveform and the second, absorption waveform; and
   k. determining the one or more physiological parameters based at least in part on the comparison, wherein the one or more physiological parameters are selected from a group consisting of atherosclerotic obstruction, vascular compliance, blood pressure, cardiac output, venous state, and vascular tone.

11. The method of claim 10, wherein the characteristic features comprise one or more of amplitudes of basis functions.

12. The method of claim 11, wherein decomposing comprises generating a histogram based on a ratio of the amplitudes of the basis functions.

13. The method of claim 11, wherein the characteristic features comprise widths of the first waveform and the second waveform.

14. The method of claim 11, wherein the characteristic features comprise magnitude of slopes of first waveform and the second waveform.

15. The method of claim 11, further comprising determining local extrema of the first waveform and the second waveform by determining time points in the first waveform and the second waveform which experience relative maximum or minimum value over a time period.

16. The method of claim 15, wherein the characteristic features comprise timing occurrences of the local extrema of the first waveform and the second waveform and wherein comparing comprises determining a temporal offset between the first waveform and the second waveform by determining a difference in the timing occurrences of the local extrema of the first waveform and the second waveform.

17. The method of claim 16, further comprising calculating differences in the timing occurrences of the local extrema of the first waveform and the second waveform to determine delays between corresponding local extrema of the first waveform and the second waveform.

18. The method of claim 17, comprising finding peaks in the first waveform and the second waveform using peak-finding algorithms, and further comprising calculating delays between corresponding peaks of the first waveform and the second waveform.

19. The method of claim 18, wherein the one or more physiological parameters comprises vascular tone, and determining the vascular tone comprises determining a degree of constriction of a blood vessel based on the delays.

20. The method of claim 10, wherein the basis functions are periodic, and wherein decomposing further comprises performing a time frequency transform of the amplitudes of the periodic basis functions.

21. The method of claim 10, wherein the characteristic features comprise amplitudes of a wavelet basis function.

22. The method of claim 21, wherein the decomposing further comprises performing a wavelet transform on the wavelet transform function.

* * * * *